(12) United States Patent
Asanuma et al.

(10) Patent No.: US 9,018,362 B2
(45) Date of Patent: Apr. 28, 2015

(54) OLIGONUCLEOTIDE AND USE THEREOF

(75) Inventors: Hiroyuki Asanuma, Nagoya (JP);
Xingguo Liang, Qingdao-shi (CN);
Hiromu Kashida, Nagoya (JP);
Hidenori Nishioka, Nagoya (JP); Taiga Fujii, Nagoya (JP); Teruchika Ishikawa, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 13/819,954

(22) PCT Filed: Jul. 22, 2011

(86) PCT No.: PCT/JP2011/066733
§ 371 (c)(1),
(2), (4) Date: Feb. 28, 2013

(87) PCT Pub. No.: WO2012/029434
PCT Pub. Date: Mar. 8, 2012

(65) Prior Publication Data
US 2013/0225797 A1    Aug. 29, 2013

(30) Foreign Application Priority Data
Aug. 31, 2010    (JP) ................. 2010-194942

(51) Int. Cl.
*C07F 9/06* (2006.01)
*C07H 21/00* (2006.01)
*C07H 21/04* (2006.01)

(52) U.S. Cl.
CPC ....... *C07H 21/00* (2013.01); *C07F 9/06* (2013.01); *C07H 21/04* (2013.01)

(58) Field of Classification Search
CPC .................................. C07F 9/06; C07H 21/00
USPC .................................................. 534/851, 727
See application file for complete search history.

(56) References Cited

U.S. PATENT DOCUMENTS

2007/0203331 A1    8/2007    Asanuma et al.
2011/0229980 A1    9/2011    Asanuma et al.

FOREIGN PATENT DOCUMENTS

JP    A-2001-346579    12/2001
(Continued)

OTHER PUBLICATIONS

Nishioka et al., "Molecular design of azobenzene derivatives for reversible photoregulation of DNA functions with visible light," *Polymer Preprints*, 2010, pp. 4957-4958, vol. 59, No. 2, Japan (w/abstract).
Nishioka et al., "Effect of the *ortho* Modification of Azobenzene on the Photoregulatory Efficiency of DNA Hybridization and the Thermal Stability of its *cis* Form," *Chemistry: A European Journal*, 2010, pp. 2054-2062, vol. 16, published by Wiley-VCH Verlag GmbH & Co. KGaA, Weinheim.
Liang et al., "Photoregulation of DNA hybridization by Introducing alkyl-modified azobenzene," *Polymer Preprints*, 2007, pp. 4838-4839, vol. 56, No. 2, Japan (w/abstract).
Liang et al., "Molecular Design of Photoresponsive DNA as Nanomaterial: Symmetric Introduction of Azobenzene for Complete ON-OFF Photoregulation," 89th *Annual Meeting of Chemical Society of Japan in Spring Koen Yokoshu II*, 2009, p. 1280, vol. 3 H6-36 (w/abstract).

(Continued)

*Primary Examiner* — Robert Havlin
(74) *Attorney, Agent, or Firm* — Oliff PLC

(57) ABSTRACT

Provided is an oligonucleotide containing an azobenzene derivative, represented by Formula (1) or (2) below:

[C30]

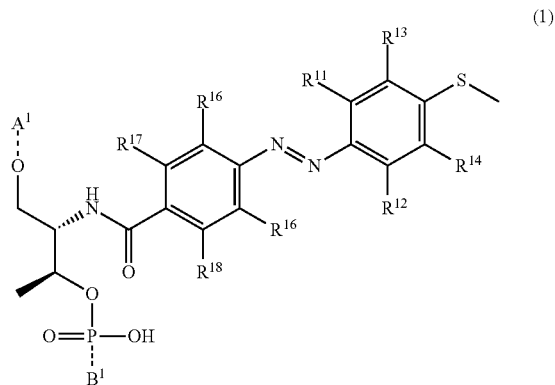

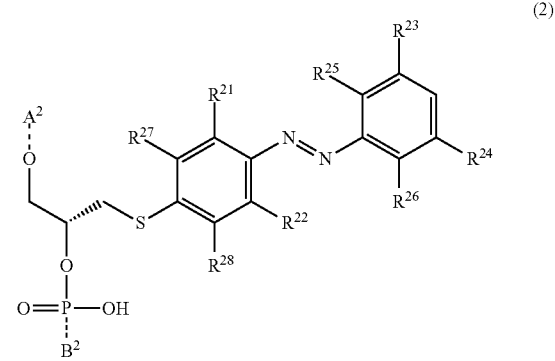

(in the formulae, $A^1$ and $A^2$ each independently represent a hydrogen atom, nucleotide or oligonucleotide, $B^1$ and $B^2$ each independently represent a hydroxyl group, nucleotide or oligonucleotide, $R^{11}$ and $R^{12}$ each independently represent a $C_{1-20}$ alkyl group, $R^{21}$ and $R^{22}$ each independently represent a hydrogen atom or $C_{1-20}$ alkyl group, and $R^{13}$ to $R^{18}$ and $R^{23}$ to $R^{28}$ each independently represent a hydrogen atom; a $C_{1-20}$ alkyl group or alkoxy group optionally substituted with a halogen atom, hydroxyl group, amino group, nitro group or carboxyl group; a $C_{2-20}$ alkenyl group or alkynyl group optionally substituted with a halogen atom, hydroxyl group, amino group, nitro group or carboxyl group; a hydroxyl group; a halogen atom; an amino group; a nitro group; or a carboxyl group).

14 Claims, 4 Drawing Sheets

(56) References Cited

FOREIGN PATENT DOCUMENTS

| | | |
|---|---|---|
| JP | A-2011-135824 | 7/2011 |
| WO | WO 01/21637 A1 | 3/2001 |
| WO | WO 2005/083073 A1 | 9/2005 |
| WO | WO 2010/001902 A1 | 1/2010 |

OTHER PUBLICATIONS

International Search Report issued in International Application No. PCT/JP2011/066733 dated Oct. 4, 2011 (w/translation).

Written Opinion of the International Searching Authority issued in International Application No. PCT/JP2011/066733 dated Oct. 4, 2011 (w/translation).

OLIGONUCLEOTIDE AND USE THEREOF

TECHNICAL FIELD

The present invention relates to an oligonucleotide, and to a photo-switching agent using the oligonucleotide. The priority claim for the present application is based on Japanese Patent Application No. 2010-194942, submitted on Aug. 31, 2010, and the entire contents of the Description of that Japanese Patent Application are incorporated by reference in this Description.

BACKGROUND ART

Techniques have been developed for controlling hybridization between oligonucleotides with complementary structures by an external stimulus. If hybridization control could be achieved, it could contribute to more precise gene detection, identification and assay, and to the development of molecular devices and molecular machines using oligonucleotides for example. pH changes, temperature changes, light irradiation and the like are used as external stimuli for controlling hybridization.

Patent Documents 1-3 describe techniques for reversibly hybridizing an oligonucleotide using light irradiation. This oligonucleotide has a residue containing an organic group such as an azobenzene or azobenzene derivative that can undergo an isomerization reaction between cis- and trans- forms in response to light irradiation. In Patent Documents 1-3, light in the ultraviolet range of less than 400 nm must be used for one or both of the cis-trans isomerization reaction and the trans-cis isomerization reaction.

CITATION LIST

Patent Literatures

Patent Document 1: Japanese Patent Application Publication No. 2001-346579
Patent Document 2: International Publication WO 01/021637
Patent Document 3: International Publication WO 05/083073

SUMMARY OF INVENTION

Technical Problem

Exposure to ultraviolet light is more damaging to living bodies than exposure to visible light. As a result, control of oligonucleotide hybridization using visible light would be desirable. To do this, it is first necessary to isomerize an oligonucleotide using visible light.

Second, there must be a sufficiently large melting temperature difference $\Delta Tm$, which is the difference in melting temperature Tm (the temperature at which an oligonucleotide complex is denatured from a double-stranded form to a single-stranded form) between structural isomers. If the melting temperature difference $\Delta Tm$ is small, hybridization control using light irradiation is less efficient.

Solution to Technical Problem

The inventors and others discovered as a result of exhaustive research that reversible isomerization of structural isomers by irradiation with light with a wavelength in the visible range could be achieved along with a high melting temperature difference $\Delta Tm$ of the structural isomers by using an oligonucleotide having an azobenzene derivative containing a sulfur atom (S) that binds to the 6-member ring of the azobenzene. Based on these findings, the present invention provides an oligonucleotide capable of photo-control of hybridization using visible light.

The present invention provides an oligonucleotide containing an azobenzene derivative, represented by Formula (1) or (2) below.

[C1]

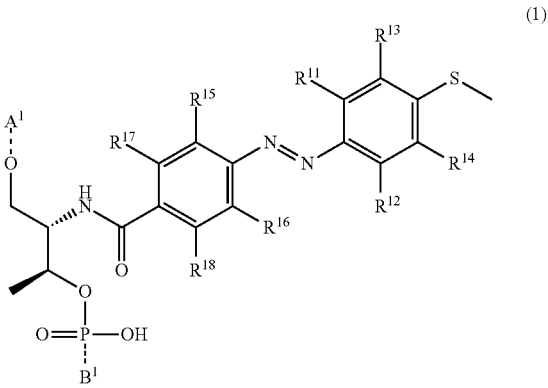

(1)

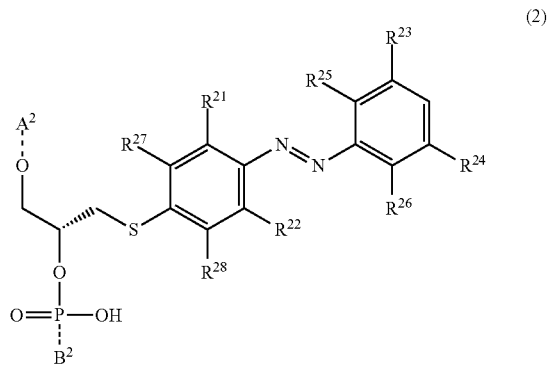

(2)

In the Formulae (1) and (2) above, $A^1$ and $A^2$ each independently represent a hydrogen atom, nucleotide or oligonucleotide, $B^1$ and $B^2$ represent hydroxyl groups, nucleotides or oligonueleotides, $R^{11}$ and $R^{12}$ each independently represent a $C_{1-20}$ alkyl group, $R^{21}$ and $R^{22}$ each independently represent a hydrogen atom or $C_{1-20}$ alkyl group, and $R^{13}$ to $R^{18}$ and $R^{23}$ to $R^{28}$ each independently represent a hydrogen atom; a $C_{1-20}$ alkyl group or alkoxy group optionally substituted with a halogen atom, hydroxyl group, amino group, nitro group or carboxyl group; a $C_{2-20}$ alkenyl group or alkynyl group optionally substituted with a halogen atom, hydroxyl group, amino group, nitro group or carboxyl group; a hydroxyl group; a halogen atom; an amino group; a nitro group; or a carboxyl group.

$R^{13}$ to $R^{18}$ and $R^{23}$ to $R^{28}$ are preferably hydrogen atoms. $R^{11}$ and $R^{12}$ are preferably methyl groups.

Moreover, the present invention provides an oligonucleotide containing an azobenzene derivative, represented by Formula (3) below.

[C2]

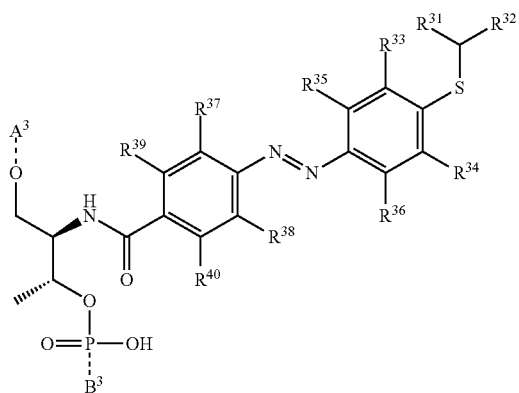

(3)

[C3]

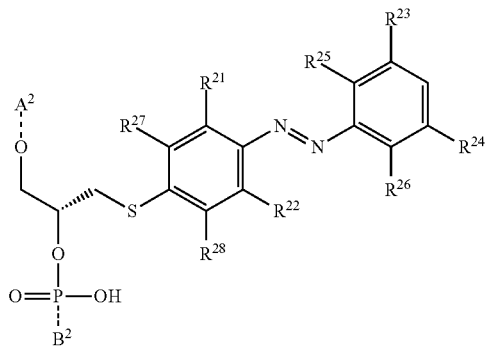

(2)

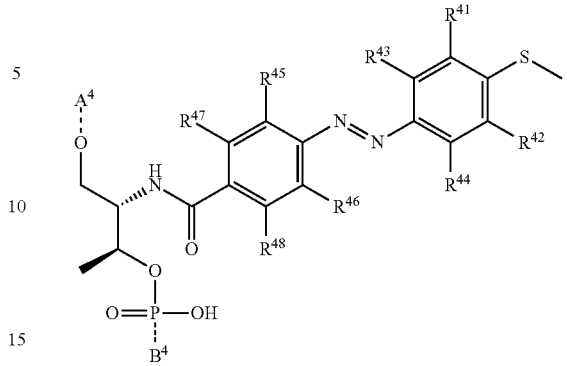

(4)

In the Formula (3) above, $A^3$ represents a hydrogen atom, nucleotide or oligonucleotide, $B^3$ represents a hydroxyl group, nucleotide or oligonucleotide, $R^{31}$ and $R^{32}$ each independently represent a $C_{1-20}$ alkyl group, or $R^{31}$ and $R^{32}$ bind with each other together with a carbon atom for linking to a sulfur atom to represent a $C_{5-40}$ cyclic alkyl group or aryl group, and $R^{33}$ to $R^{40}$ each independently represent a hydrogen atom; a $C_{1-20}$ alkyl group or alkoxy group optionally substituted with a halogen atom, hydroxyl group, amino group, nitro group or carboxyl group; a $C_{2-20}$ alkenyl group or alkynyl group optionally substituted with a halogen atom, hydroxyl group, amino group, nitro group or carboxyl group; a hydroxyl group; a halogen atom; an amino group; a nitro group; or a carboxyl group.

$R^{31}$ and $R^{32}$ preferably bind to each other together with a carbon atom for linking to a sulfur atom to form a cyclohexyl group or adamantyl group. Alternatively, it is desirable for $R^{31}$ and $R^{32}$ to each independently be a $C_{1-4}$ alkyl group, while $R^{33}$ to $R^{40}$ are hydrogen atoms. In this case, it is especially desirable for both $R^{31}$ and $R^{32}$ to be methyl groups.

The present invention also provides a photo-switching agent which is provided with the aforementioned oligonucleotide, and by which the formation and dissociation of a double strand can be controlled by visible light irradiation.

The present invention also provides a photo-switching agent by which the formation and dissociation of a double strand can be controlled by visible light irradiation, and which is provided with a pair of oligonucleotides having complementary sequences that form a complex, with each of the pair of oligonucleotides being provided with at least one azobenzene derivative represented by Formula (2) or (4) below in a pairing position.

In the Formulae (2) and (4) above, $A^2$ and $A^4$ each independently represent a hydrogen atom, nucleotide or oligonucleotide, $B^2$ and $B^4$ each independently represent a hydroxyl group, nucleotide or oligonucleotide, $R^{21}$ and $R^{22}$ each independently represent a hydrogen atom or $C_{1-20}$ alkyl group, and $R^{23}$ to $R^{28}$ and $R^{41}$ to $R^{48}$ each independently represent a hydrogen atom; a $C_{1-20}$ alkyl group or alkoxy group optionally substituted with a halogen atom, hydroxyl group, amino group, nitro group or carboxyl group; a $C_{2-20}$ alkenyl group or alkynyl group optionally substituted with a halogen atom, hydroxyl group, amino group, nitro group or carboxyl group; a hydroxyl group; a halogen atom; an amino group; a nitro group; or a carboxyl group.

$R^{43}$ and $R^{44}$ are preferably methyl groups or hydrogen atoms, and $R^{41}$, $R^{42}$ and $R^{45}$ to $R^{48}$ are preferably hydrogen atoms.

Each of the aforementioned pair of oligonucleotides preferably has two or more adjacent azobenzene derivatives on either side of two or more nucleotides.

An azobenzene derivative that can be used favorably for manufacturing the oligonucleotide of the present invention can also be provided. The present invention provides the azobenzene derivative represented by Formula (11) below.

[C4]

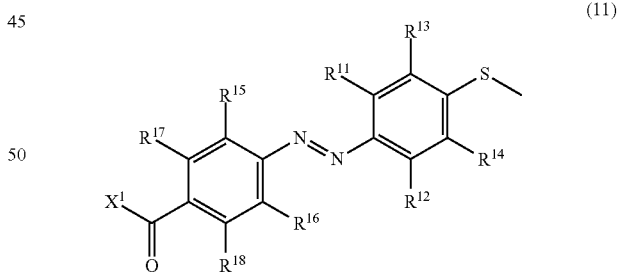

(11)

In the Formula (11) above, $X^1$ represents either a hydroxyl group or a group represented by Formula (12) below, and $R^{12}$ each independently represent a $C_{1-20}$ alkyl group, and $R^{13}$ to $R^{18}$ each independently represent a hydrogen atom; a $C_{1-20}$ alkyl group or alkoxy group optionally substituted with a halogen atom, hydroxyl group, amino group, nitro group or carboxyl group; a $C_{2-20}$ alkenyl group or alkynyl group optionally substituted with a halogen atom, hydroxyl group, amino group, nitro group or carboxyl group; a hydroxyl group; a halogen atom; an amino group; a nitro group; or a carboxyl group.

[C5]

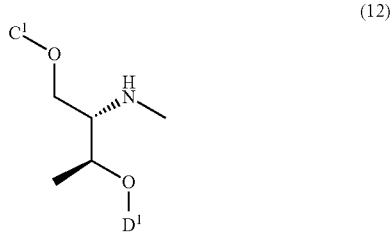
(12)

In the Formula (12) above, $C^1$ represents a hydrogen atom or hydroxyl protecting group, and $D^1$ represents a hydrogen atom, a hydroxyl protecting group, a phosphoramidite group or a linking group that is bound or to be bound to a solid-phase carrier.

The present invention also provides an azobenzene derivative represented by Formula (13) below.

[C6]

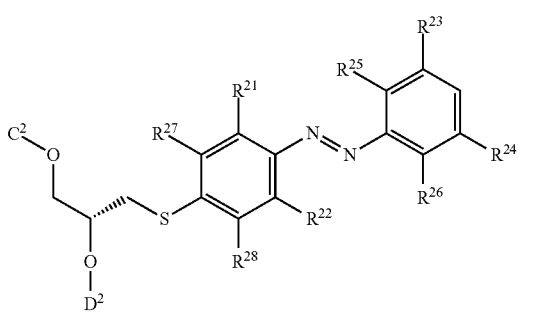
(13)

In the Formula (13) above, $C^2$ represents a hydrogen atom or hydroxyl protecting group, $D^2$ represents a hydrogen atom, a hydroxyl protecting group, a phosphoramidite group or a linking group that is bound or to be bound to a solid-phase carrier, $R^{21}$ and $R^{22}$ each independently represent a hydrogen atom or $C_{1-20}$ alkyl group, and $R^{23}$ to $R^{28}$ each independently represent a hydrogen atom; a $C_{1-20}$ alkyl group or alkoxy group optionally substituted with a halogen atom, hydroxyl group, amino group, nitro group or carboxyl group; a $C_{2-20}$ alkenyl or alkynyl group optionally substituted with a halogen atom, hydroxyl group, amino group, nitro group or carboxyl group; a hydroxyl group; a halogen atom; an amino group; a nitro group; or a carboxyl group.

The present invention also provides an azobenzene derivative represented by Formula (14) below.

[C7]

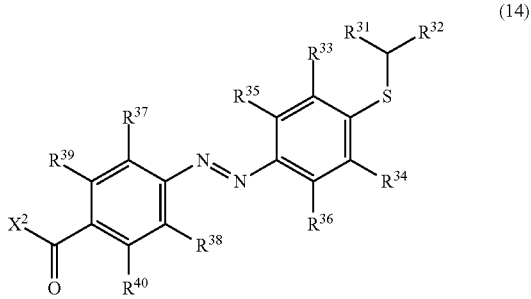
(14)

In the Formula (14) above, $X^2$ represents a hydroxyl group or a group represented by Formula (15) below, $R^{31}$ and $R^{32}$ each independently represent a $C_{1-20}$ alkyl group, or $R^{31}$ and $R^{32}$ bind with each other together to represent a $C_{5-40}$ cyclic alkyl group or aryl group with a carbon atom for linking to a sulfur atom, and $R^{33}$ to $R^{40}$ each independently represent a hydrogen atom; a $C_{1-20}$ alkyl group or alkoxy group optionally substituted with a halogen atom, hydroxyl group, amino group, nitro group or carboxyl group; a $C_{2-20}$ alkenyl group or alkynyl group optionally substituted with a halogen atom, hydroxyl group, amino group, nitro group or carboxyl group; a hydroxyl group; a halogen atom; an amino group; a nitro group; or a carboxyl group.

[C8]

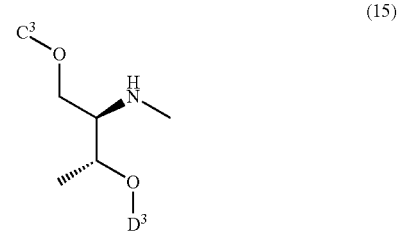
(15)

In the Formula (15) above, $C^3$ represents a hydrogen atom or hydroxyl protecting group, and $D^3$ represents a hydrogen atom, a hydroxyl protecting group, a phosphoramidite group, or a linking group that is bound or to be bound to a solid-phase carrier.

DESCRIPTION OF EMBODIMENTS

Figure 1:
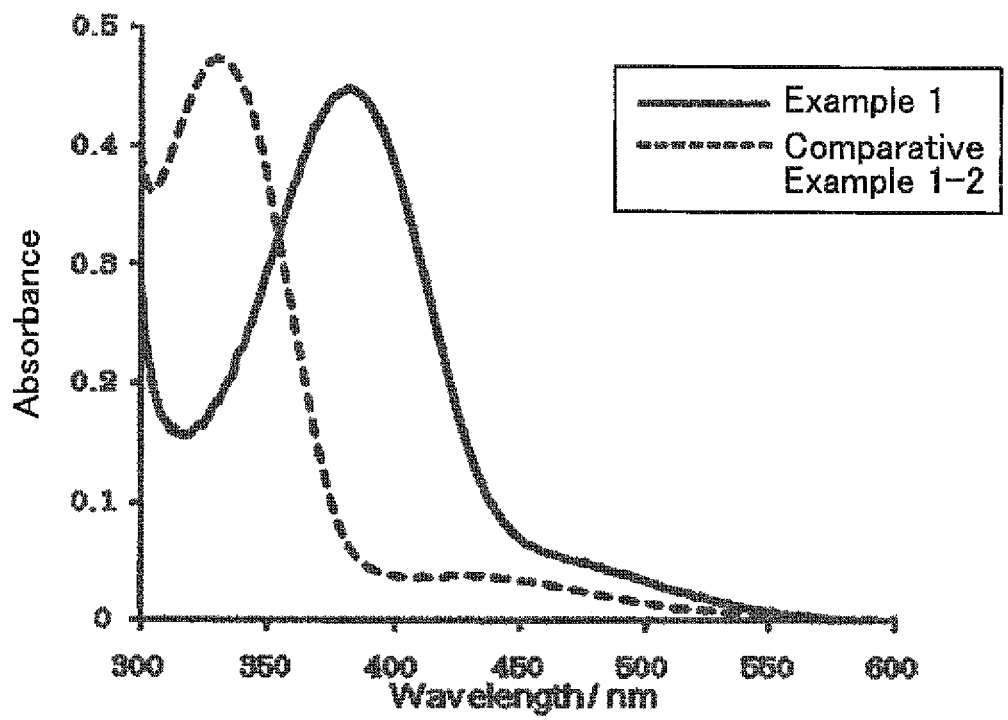
FIG. 1 shows ultraviolet and visible light absorption spectra of Example 1.

The present invention provides an oligonucleotide whereby the isomerization reaction of structural isomers can be controlled by irradiation with light having a wavelength in the visible light range, as well as a photo-switching agent for hybridization. More specifically, it provides an oligonucleotide whereby structural isomers can be reversibly isomerized by irradiation with light having a wavelength in the visible light range, and having a large melting temperature difference ΔTm of the structural isomers. In the present invention, the visible light range is a range having a wavelength of at least 400 nm.

In this Description, an oligonucleotide may be any nucleotide polymer comprising the specific structural unit disclosed in this Description, and the number of nucleotide residues is not particularly limited. The nucleotides making up the oligonucleotide may be ribonucleotides or deoxyribonucleotides, or a combination of both. Thus, the oligonucleotide disclosed in this Description encompasses DNA, mRNA, tRNA, and various kinds of functional RNA. Moreover, the double strand of the oligonucleotide encompasses DNA/DNA double strands, DNA/RNA double strands and RNA/RNA double strands.

When an oligonucleotide having the specific unit disclosed in this Description is configured so that it can assume a double-stranded structure based on its complementary nucleotide sequence, the formation and dissociation of the double strand can be controlled by visible light irradiation, at least in the part that contains the specific unit. Formation and dissociation of DNA double strands is strongly associated with gene expression, gene replication, gene repair and various other functions involving genes. The same applies to DNA elongation reactions using polymerase such as DNA polymerase. Thus, the oligonucleotide disclosed in this Description is useful as an agent for controlling formation and dissociation of oligonucleotide double strands, and also as a DNA elongation reaction photo-switching agent and a gene function photo-switching agent that allows the formation and dissociation of double strands to be controlled by visible light irradiation.

As shown in the Formulae (1) to (4) above, the oligonucleotide of the present invention comprises an azobenzene derivative bound via a linker to a backbone containing a phosphate ester, with the azobenzene derivative being incorporated into the oligonucleotide as a side chain. The azobenzene derivative encompasses an azobenzene derivative containing a sulfur atom bound to the 6-member ring of azobenzene. Any number of molecules of the azobenzene derivative may be contained in the oligonucleotide as long as one or more molecules thereof are contained. One molecule per 1 to 5 nucleotides is preferred, and one molecule per 2 to 4 nucleotides is especially preferred.

The oligonucleotides shown in the Formulae (1) to (3) above have structural cis- and trans-isomers due to the azo bond of the azobenzene derivative, and a reversible isomerization reaction between cis- and trans-isomers can be induced by irradiation with light in the visible light range.

When an oligonucleotide shown in the Formulae (1) to (3) above hybridizes with an oligonucleotide having a complementary structure (called a complementary oligonucleotide in this Description) to form a complex, the stability of the complex differs according to whether the azobenzene derivative of the oligonucleotide of the present invention is in cis- or trans-form. Therefore, the isomerization reaction can be controlled by irradiation with visible light when hybridizing an oligonucleotide shown in the Formulae (1) to (3) above with its complementary oligonucleotide. Specifically, a pair of oligonucleotides can be hybridized by irradiation with specific visible light, and the resulting complex formed from the pair of oligonucleotides can be de-hybridized by irradiation with a different specific visible light. Because only visible light is used, with no need to use ultraviolet light, hybridization of a pair of oligonucleotides can be controlled without damage to cells or enzymes. In the present invention, both of the pair of complementary oligonucleotides may be oligonucleotides shown in the Formulae (1) to (3) above.

In the oligonucleotides shown in the Formulae (1) to (3) above, there is a sufficient large melting temperature difference $\Delta Tm$, which is the difference in melting temperature (temperature at which an oligonucleotide complex is denatured from a double-stranded structure to a single-stranded state) between the melting temperature of the cis-isomer and the melting temperature of the trans-isomer. As a result, the reliability of hybridization control by visible light is improved because trans-cis isomerization produces a significant difference in the stability of the double strand.

The inventors and others discovered as a result of exhaustive research that an isomerization reaction can be achieved with visible light in some cases only when both of a pair of oligonucleotides having complementary sequences contain azobenzene derivatives, making them effective as a photo-switching agent. It was also discovered that the same effect could be obtained even using a pair of the oligonucleotides shown in the Formula (1) or (2) above. That is, when each of a pair of oligonucleotides has at least one azobenzene derivative represented by the Formula (2) or (4) above in a pairing position, an isomerization reaction using visible light can be achieved as in the case of the oligonucleotides shown by the Formulae (1) to (3) above, with a sufficiently large melting temperature difference $\Delta Tm$.

It is also possible to provide an azobenzene derivative that can be used favorably for manufacturing the oligonucleotide of the present invention. The azobenzene derivatives shown in the Formulae (11), (13) and (14) above are intermediates for the oligonucleotides shown in the Formulae (1) to (3) above, and can be used favorably for manufacturing the oligonucleotides shown in Formulae (1) to (3) above. Constituents in the Formulae (11), (13) and (14) above that are the same as in Formulae (1) to (3) above ($R^{11}$ to $R^{18}$, $R^{21}$ to $R^{28}$, $R^{31}$ to $R^{40}$, etc.) have that same configurations as in the Formulae (1) to (3) above. Thus, applicable structures and preferred structures in the Formulae (1) to (3) in this Description can be applied to the Formulae (11), (13) and (14) above.

In the Formulae (12), (13) and (15) above, $C^1$ to $C^3$ represent hydrogen atoms or hydroxyl protecting groups. The hydroxyl protecting groups are not particularly limited, and conventionally known hydroxyl protecting groups can be used. Examples include fluorenylmethoxycarbonyl (FMOC) groups, dimethoxytrityl (DMT) groups, tert-butyldimethylsilyl (TBDMS) groups, monomethoxytrityl groups, trifluoroacetyl groups, levulinyl groups or silyl groups. Trityl groups are preferred as protecting groups, and may be selected for example from monomethyltrityl (MMT), dimethoxytrityl (DMT) and tert-butyldimethylsilyl (TBDMS) groups.

$D^1$ to $D^3$ represent hydrogen atoms, hydroxyl protecting groups, phosphoramidite groups or linking groups that are bound or to be bound to a solid-phase carrier. A compound (amidite compound) in which $D^1$ to $D^3$ are phosphoramidite groups can be used as a phosphoramidite reagent to synthesize an oligonucleotide by the phosphoramidite method. In the present invention, an phosphoramidite group encompasses any that can be used in such a phosphoramidite method, without any particular limitations, but may be represented by Formula (16) below for example.

[C9]

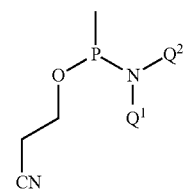

(16)

In Formula (16) above, $Q^1$ and $Q^2$ each independently represent a branched or linear $C_{1-5}$ alkyl group, and may be the same or different. $Q^1$ and $Q^2$ are not particularly limited, but preferred examples include isopropyl groups.

In the Formulae (12), (13) and (15) above, those compounds in which $D^1$ to $D^3$ are linking groups that will be bound to a solid-phase carrier will be supported on a solid-phase carrier by binding between these linking groups and amino groups or other specific functional groups on the solid-phase carrier. Moreover, in the Formulae (12), (13) and (15) above, those compounds in which $D^1$ to $D^3$ are linking groups that are bound to a solid-phase carrier can be used as starting materials for various kinds of solid-phase nucleic acid synthesis because the oligonucleotide is bound to a solid-phase carrier via the linking groups. For example, an oligonucleotide represented by Formulae (1) to (3) containing an azobenzene derivative can be manufactured with a DNA synthesizer using this starting material.

Various embodiments and examples of the present invention are explained below.

(First Embodiment)

The oligonucleotide of the first embodiment is explained as one embodiment of the present invention. The oligonucleotide of the first embodiment contains an azobenzene derivative represented by Formula (1) or (2) above. In Formula (1) above, the azobenzene derivative is bound to a backbone via a D-threoninol linker. The linker and a methylthio group are bound in positions that are symmetrical relative the azo group binding the two benzene rings of the azobenzene derivative, and are each bound in the para position relative to the azo group. The azobenzene derivative is further provided with two alkyl groups ($R^{11}$ and $R^{12}$ in Formula (1) above) on the benzene ring having the bound methylthio group, and these two alkyl groups are both bound in ortho positions relative to the azo group. In Formula (2) above, meanwhile, the azobenzene derivative and linker are bound via a sulfur atom (S). The sulfur atom is bound in the para position relative to the azo group. The azobenzene derivative may also be further provided with two alkyl groups on the benzene ring with the bound sulfur atom, and these two alkyl groups are preferably each bound in an ortho position relative to the azo group (positions of $R^{21}$ and $R^{22}$ in Formula (2) above).

In Formulae (1) and (2) above, $A^1$ and $A^2$ each independently represent a hydrogen atom, nucleotide or oligonucleotide, while $B^1$ and $B^2$ each independently represent a hydroxyl group, nucleotide or oligonucleotide. $R^{13}$ to $R^{18}$ and $R^{23}$ to $R^{28}$ each independently represent a hydrogen atom; a $C_{1-20}$ alkyl group or alkoxy group optionally substituted with a halogen atom, hydroxyl group, amino group, nitro group or carboxyl group; a $C_{2-20}$ alkenyl group or alkynyl group optionally substituted with a halogen atom, hydroxyl group, amino group, nitro group or carboxyl group; a hydroxyl group; a halogen atom; an amino group; a nitro group; or a carboxyl group.

$R^{13}$ to $R^{18}$ and $R^{23}$ to $R^{28}$ are preferably hydrogen atoms or alkyl groups, and most preferably hydrogen atoms. The alkyl groups preferably have 1 to 8, or more preferably 1 to 4, or still more preferably 1 to 3 carbon atoms, or most preferably are methyl groups.

$R^{11}$ and $R^{12}$ each independently represent a $C_{1-20}$ alkyl group. $R^{21}$ and $R^{22}$ are preferably hydrogen atoms or linear alkyl groups, and the alkyl groups preferably have 1 to 8, or more preferably 1 to 4, or still more preferably 1 to 3 carbon atoms, or most preferably are methyl groups.

In general, the maximum absorption wavelength of an azobenzene can be increased by introducing an electron-releasing substituent such as an alkylthio group into the para position of the azo group, but with the side effect of promoting cis-to-trans thermal isomerization. Such cis-to-trans isomerization not caused by light irradiation is undesirable because it is an unintended switch. Thus, it is desirable to suppress thermal isomerization of the cis-form as much as possible. In Formula (1) above, the two alkyl groups ($R^{11}$, $R^{12}$) in the ortho positions (relative to the azo group) on the benzene ring having the methylthio group have the effect of suppressing cis-to-trans thermal isomerization while contributing to the stability of the double strand in the trans-form.

In Formula (2) above, $R^{21}$ and $R^{22}$ each independently represent a hydrogen atom or $C_{1-20}$ alkyl group. $R^{21}$ and $R^{22}$ are preferably hydrogen atoms or linear alkyl groups, and each alkyl group preferably has 1 to 8, or more preferably 1 to 4, or still more preferably 1 to 3 carbon atoms, or is most preferably a methyl group. As in Formula (1) above, the alkyl groups introduced here have the effect of suppressing cis-to-trans thermal isomerization while contributing to the stability of the double strand in the trans-form. $R^{21}$ and $R^{22}$ may also be hydrogen atoms.

The oligonucleotide of the first embodiment has structural cis- and tran-isomers according to the azo bond of the azobenzene derivative, and a reversible cis-trans isomerization reaction can be accomplished by irradiation with light in the visible light range.

The oligonucleotide of the first embodiment is more stable when the azobenzene derivative is in the trans-form, which has a planar structure, and less stable when in the cis-form, which has a non-planar structure. During hybridization between the oligonucleotide of the first embodiment and an oligonucleotide having a structure complementary thereto (hereunder called a complementary oligonucleotide in this Description), if the pair of oligonucleotides is irradiated with visible light at a specific wavelength, the azobenzene derivative of the oligonucleotide of the first embodiment is isomerized into the trans-form, and intercalates between base pairs of the pair of oligonucleotides. The pair of oligonucleotides is reciprocally stacked by the trans-isomer of the azobenzene derivative, thereby stabilizing the double-stranded oligonucleotide complex.

When the complex formed by the hybridized pair of oligonucleotides is irradiated with visible light at a specific wavelength, the azobenzene derivative of the oligonucleotide of the first embodiment is isomerized into the cis-form. Because the cis-form has a non-planar structure, steric hindrance occurs with the base pairs of the pair of oligonucleotides, destabilizing the double-stranded oligonucleotide complex.

Hybridization with a complementary oligonucleotide can be controlled by controlling the isomerization reaction of the azobenzene derivative of the oligonucleotide of the first embodiment by irradiation with visible light.

Moreover, in the oligonucleotide represented by Formula (1) or (2) above, there is a sufficiently large melting temperature difference $\Delta Tm$ between the melting temperature of the cis-form and the melting temperature of the trans-form. The reliability of control with visible light is thereby improved. In particular, in the oligonucleotide represented by Formula (2) above having an azobenzene derivative, at least one of $R^{21}$ and $R^{22}$ is preferably an alkyl group from the standpoint of achieving a greater $\Delta Tm$. In the oligonucleotide represented by Formula (1) or (2) above, the melting temperature of the cis-form is lower than the melting temperature of the trans-form. That is, the oligonucleotides represented by Formulae (1) and (2) above act as forward switches.

The azobenzene derivative represented by Formula (11) above is an intermediate for manufacturing the oligonucleotide of Formula (1) above, and can be used favorably to manufacture Formula (1) above. For example, the oligonucleotide of Formula (1) above can be manufactured favorably with a DNA synthesizer or the like, using as an amidite monomer an azobenzene derivative in which $X^1$ in Formula (11) is represented by Formula (12) above, $C^1$ in the formula is a hydroxyl protecting group (such as a dimethoxytrityl group), and $D^1$ is a phosphoramidite group (for example, the phosphoramidite group represented by Formula (16) above, in which $Q^1$ and $Q^2$ are isopropyl groups).

The azobenzene derivative of Formula (13) above is an intermediate for manufacturing the oligonucleotide of Formula (2) above, and can be used favorably for manufacturing Formula (2) above. For example, the oligonucleotide of Formula (2) above can be manufactured favorably with a DNA synthesizer or the like, using as an amidite monomer an azobenzene derivative represented by Formula (13) above in which $C^2$ is a hydroxyl protecting group (such as a dimethoxytrityl group), and $D^2$ is a phosphoramidite group (for example, the phosphoramidite group represented by Formula (16) above, in which $Q^1$ and $Q^2$ are isopropyl groups).

(Second Embodiment)

The oligonucleotide of the second embodiment is explained as another embodiment of the present invention. The second embodiment relates to the oligonucleotide represented by Formula (3) above, which contains an azobenzene derivative. As shown in Formula (3) above, the azobenzene derivative is bound to a backbone via an L-threoninol linker, and the linker and an alkylthio group are bound in positions that are symmetrical relative to the azo group binding the two benzene rings of the azobenzene derivative, and are each bound in the para position relative to the azo group. As shown in Formula (3) above, the alkylthio group comprises a CH group for binding to a sulfur atom, and the CH group is bound to two alkyl groups $R^{31}$ and $R^{32}$.

In Formula (3) above, $A^3$ represents a hydrogen atom, nucleotide or oligonucleotide, $B^2$ represents a hydroxyl group, nucleotide or oligonucleotide, $R^{31}$ and $R^{32}$ each independently represent a $C_{1-20}$ alkyl group, or $R^{31}$ and $R^{32}$ bind to each other together with a carbon atom for linking to a sulfur atom to form a $C_{5-40}$ cyclic alkyl group or aryl group, and $R^{33}$ to $R^{40}$ each independently represent a hydrogen atom; a $C_{1-20}$ alkyl group or alkoxy group optionally substituted with a halogen atom, hydroxyl group, amino group, nitro group or carboxyl group; a $C_{2-20}$ alkenyl group or alkynyl group optionally substituted with a halogen atom, hydroxyl group, amino group, nitro group or carboxyl group; a hydroxyl group; a halogen atom; an amino group; a nitro group; or a carboxyl group.

$R^{31}$ and $R^{32}$ may be methyl groups, ethyl groups, propyl groups or other linear alkyl groups, or may constitute a cyclic alkyl group or phenyl or other aryl group containing $R^{31}$, $R^{32}$ and a CH group for binding to a sulfur atom. When one of the alkyl groups binding to a sulfur atom is hydrogen (CH group), the bond binding the CH group and the sulfur atom is easily positioned on the same plane as the benzene ring even when $R^{31}$ and $R^{32}$ have such bulky structures, and the maximum absorption wavelength of the oligonucleotide of Formula (3) above is increased by an electron releasing effect. The bulky structure consisting of the $R^{31}$, $R^{32}$ and the CH group for binding to the sulfur atom is preferably a cyclic hydrocarbon group, and a saturated cyclic hydrocarbon group is more preferred. Specific, $R^{31}$, $R^{32}$ and the CH group for binding to the sulfur atom preferably constitute a phenyl group, naphthyl group, anthryl group, phenanthryl group, phenalenyl group, biphenyl group, cyclopropyl group, cyclobutyl group, cyclopentyl group, cyclohexyl group, cycloheptyl group, cyclooctyl group, adamantyl group, diamantyl group or triamantyl group or the like, or such a group with a hydroxyl group, carboxyl group, nitro group, amino group, alkyl group, aryl group or other substituent substituted for a hydrogen atom, and a cyclohexyl group or adamantyl group is especially desirable. From the standpoint of improving photo-control efficiency, $R^{31}$ and $R^{32}$ are preferably bulkier, while from the standpoint of ease of manufacture, $R^{31}$ and $R^{32}$ in Formula (3) above are preferably $C_{1-20}$ alkyl groups, and the alkyl groups preferably have 1 to 8 or more preferably 1 to 4 or still more preferably 1 to 3 carbon atoms, or most preferably are methyl groups.

$R^{33}$ to $R^{40}$ each independently represent a hydrogen atom; a $C_{1-20}$ alkyl group or alkoxy group optionally substituted with a halogen atom, hydroxyl group, amino group, nitro group or carboxyl group; a $C_{2-20}$ alkenyl group or alkynyl group optionally substituted with a halogen atom, hydroxyl group, amino group, nitro group or carboxyl group; a hydroxyl group; a halogen atom; an amino group; a nitro group; or a carboxyl group. $R^{33}$ to $R^{40}$ are preferably hydrogen atoms or alkyl groups, and hydrogen atoms are especially desirable. The alkyl groups preferably have 1 to 8 or more preferably 1 to 4 or still more preferably 1 to 3 carbon atoms, or most preferably are methyl groups.

The oligonucleotide of the second embodiment has structural cis- and trans-isomers due to the azo bond of the azobenzene derivative, and a reversible isomerization reaction between cis- and trans-isomers can be induced by irradiation with light in the visible light range.

The oligonucleotide of the second embodiment is more stable when the azobenzene derivative is in the cis-form, which has a non-planar structure, and less stable when in the trans-form, which has a planar structure. During hybridization between the oligonucleotide of the second embodiment and its complementary oligonucleotide, if the pair of oligonucleotides is irradiated with visible light at a specific wavelength, the azobenzene derivative of the oligonucleotide of the second embodiment is isomerized into the cis-form, and groove binds with the double strand of paired oligonucleotides, thereby stabilizing the double-stranded oligonucleotide complex. In the case of the trans-form, on the other hand, the double-stranded oligonucleotide complex is destabilized by the effect of the L-threoninol used as a linker and by steric hindrance between the bulky $R^{31}$ and $R^{32}$ and the oligonucleotide of the complementary strand.

When a complex of a pair of hybridized oligonucleotides is irradiated with visible light at a specific wavelength, the azobenzene derivative of the oligonucleotide of the second embodiment is isomerized into the trans-form. The oligonucleotide complex is destabilized when the azobenzene derivative is isomerized into the trans-form.

Hybridization with a complementary oligonucleotide can be controlled by controlling the isomerization reaction of the azobenzene derivative of the oligonucleotide of the second embodiment by irradiation with visible light.

Moreover, in the oligonucleotide represented by Formula (3) above, there is a sufficiently large melting temperature difference $\Delta Tm$ between the melting temperature of the cis-form and the melting temperature of the trans-form. The reliability of control with visible light is thereby improved. Note that in the oligonucleotide represented by Formula (3) above, the melting temperature of the cis-form is higher than the melting temperature of the trans-form. That is, unlike those of Formulae (1) and (2) above, the oligonucleotide represented by Formula (3) above acts as a reverse switch. When using the oligonucleotide represented by Formula (3) above, moreover, the absolute value of $\Delta Tm$ can be made higher than when using the oligonucleotide represented by Formula (2) above, making it possible to provide an oligonucleotide with greater photo-control ability.

The azobenzene derivative represented by Formula (14) above is an intermediate for manufacturing the oligonucleotide of Formula (3) above, and can be used favorably to manufacture Formula (3) above. For example, the oligonucleotide of Formula (3) above can be manufactured favorably with a DNA synthesizer or the like, using as an amidite monomer an azobenzene derivative in which $X^2$ in Formula (14) is represented by Formula (15) above, $C^3$ in the formula is a hydroxyl protecting group (such as a dimethoxytrityl group), and $D^3$ is a phosphoramidite group (for example, the phosphoramidite group represented by Formula (16) above, in which $Q^1$ and $Q^2$ are isopropyl groups).

(Third Embodiment)

The third embodiment is explained as another embodiment of the present invention. The third embodiment relates to a photo-switching agent, provided with a pair of oligonucleotides having complementary sequences that form a complex. Each of the pair of oligonucleotides has at least one azobenzene derivative represented by Formula (2) or (4) above in a pairing position. The pair of oligonucleotides form a complex in such a way that their azobenzene derivatives associate. Each of the pair of oligonucleotides preferably comprises two or more adjacent azobenzene derivatives on either side of two or more nucleotides.

An oligonucleotide of Formula (2) above that can be used favorably in the third embodiment is similar to an oligonucleotide that can be used favorably in the first embodiment.

Figure 3:
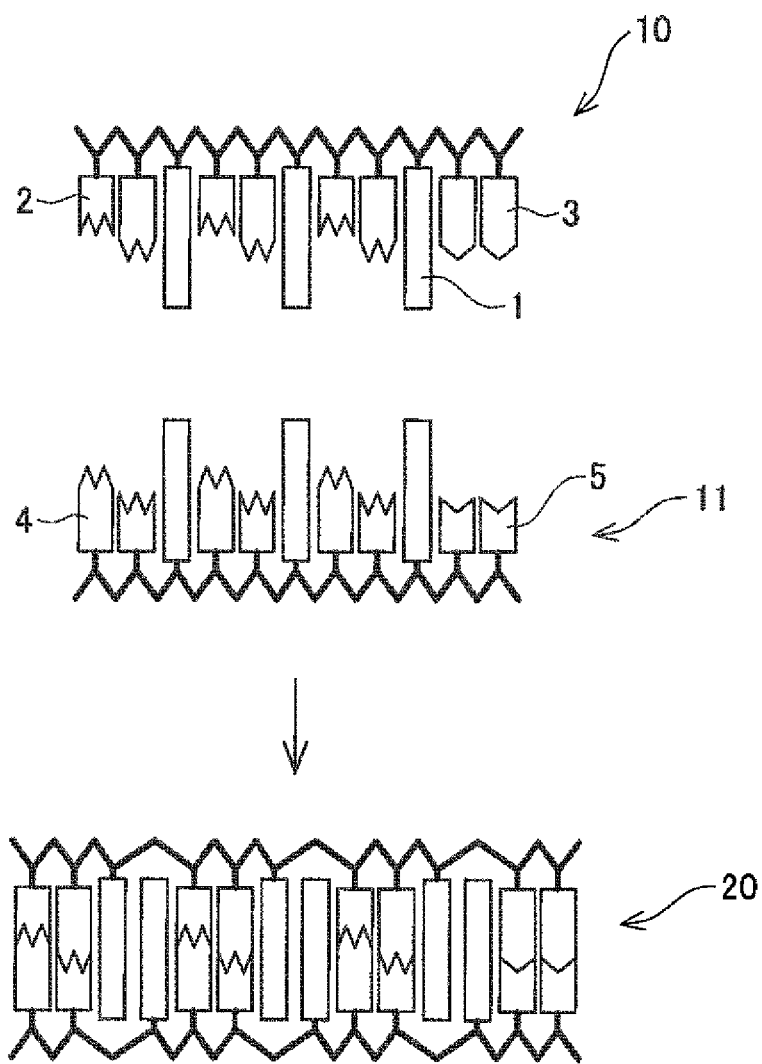
FIG. 3 is a conceptual view of a pair of oligonucleotides of Example 3, and a complex thereof.

The third embodiment is explained in detail with reference to FIG. 3. FIG. 3 illustrates one example of a pair of oligonucleotides of the third embodiment, and a complex thereof. As shown in FIG. 3, the pair of oligonucleotides 10, 11 having complementary structures are provided with residues 1 of the azobenzene derivative represented by Formula (2) or (4), complementary natural nucleotides 2, 4, and complementary natural nucleotides 3, 5. When multiple residues 1 are contained in a single oligonucleotide as in the case of oligonucleotides 10, 11, adjacent multiple residues 1 are separated by two or more nucleotides. When a pair of the oligonucleotides 10 form a complex 20, the residues 1 of the oligonucleotide 10 associate with the residues 1 of the oligonucleotide 11.

In Formula (4) above, $A^4$ represents a hydrogen atom, nucleotide or oligonucleotide, $B^4$ represents a hydroxyl group, nucleotide or oligonucleotide, and $R^{41}$ to $R^{48}$ each independently represent a hydrogen atom; a $C_{1-20}$ alkyl group or alkoxy group optionally substituted with a halogen atom, hydroxyl group, amino group, nitro group or carboxyl group; a $C_{2-20}$ alkenyl group or alkynyl group optionally substituted with a halogen atom, hydroxyl group, amino group, nitro group or carboxyl group; a hydroxyl group; a halogen atom; an amino group; a nitro group; or a carboxyl group.

$R^{41}$ to $R^{48}$ are preferably hydrogen atoms or alkyl groups, and the alkyl groups have preferably 1 to 8 or more preferably 1 to 4 or still more preferably 1 to 3 carbon atoms, or are most preferably methyl groups. It is especially desirable that $R^{43}$ and $R^{44}$ be methyl groups or hydrogen atoms, and especially desirable that $R^{41}$, $R^{42}$ and $R^{45}$ to $R^{48}$ all be hydrogen atoms.

As shown in Formula (4), the azobenzene derivative is bound to the backbone via a D-threoninol linker. The linker and a methylthio group are bound in symmetrical positions relative to the azo group that binds the two benzene rings of the azobenzene derivative, and are each bound in a para position relative to the azo group.

The pair of oligonucleotides of the third embodiment has structural cis- and trans-isomers due to the azo bond of the azobenzene derivative, and a reversible isomerization reaction between cis- and trans-isomers can be induced by irradiation with light in the visible light range. The oligonucleotide of Formula (2) above is not explained because it is similar to that of the first embodiment.

The pair of oligonucleotides of the third embodiment is more stable when the azobenzene derivative is in the trans-form, which has a planar structure, and less when in the cis-form, which has a non-planar structure. During hybridization between the pair of oligonucleotides of the third embodiment, if the pair of oligonucleotides is irradiated with visible light at a specific wavelength, the azobenzene derivative of the oligonucleotide of Formula (4) above is isomerized into the trans-form, and intercalates between base pairs of the pair of oligonucleotides. The pair of oligonucleotides is reciprocally stacked by the trans-isomer of the azobenzene derivative, thereby stabilizing the double-stranded oligonucleotide complex.

When the complex formed by the hybridized pair of oligonucleotides is irradiated with visible light at a specific wavelength, the azobenzene derivatives of the pair of oligonucleotides of the third embodiment are isomerized into the cis-form. Because the cis-form has a non-planar structure, steric hindrance occurs with base pairs of the pair of oligonucleotides, destabilizing the double-stranded oligonucleotide complex.

Hybridization of a pair of oligonucleotides can be controlled by controlling the isomerization reaction of the azobenzene derivative of the oligonucleotide of Formula (4) above by irradiation with visible light.

With a pair of oligonucleotides both represented by Formula (4) above, there is a sufficiently large melting temperature difference $\Delta Tm$ between the melting temperature of the cis-form and the melting temperature of the trans-form. The reliability of hybridization control using visible light is thereby improved. In the oligonucleotide represented by Formula (4) above, the melting temperature of the cis-form is lower than the melting temperature of the trans-form. That is, as with Formulae (1) and (2) above, the oligonucleotide represented by Formula (4) acts as a forward switch. Moreover, the absolute value of $\Delta Tm$ can be made larger by using the oligonucleotide represented by Formula (4) above than by using the oligonucleotide represented by Formula (2) above, making it possible to provide an oligonucleotide with even greater photo-control ability.

EXAMPLES

The present invention is explained below using specific examples, but the present invention is not limited by these specific examples.

Example 1

In Example 1, an oligonucleotide represented by Formula (Ia) below containing a methylthioazobenzene derivative is explained as an example of the oligonucleotide represented by Formula (1) above.

[C10]

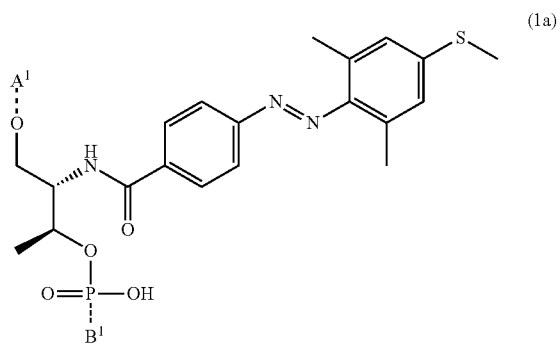

(1a)

(Oligonucleotide manufacture)

The oligonucleotide of Formula (1a) above was synthesized in accordance with the scheme of Formula (5) below. The Compounds 2-1 to 2-6 used in synthesis are shown in Formula (5) below. The Compounds 2-2 to 2-6 constitute an example of the azobenzene derivative of Formula (11) above.

[C11]
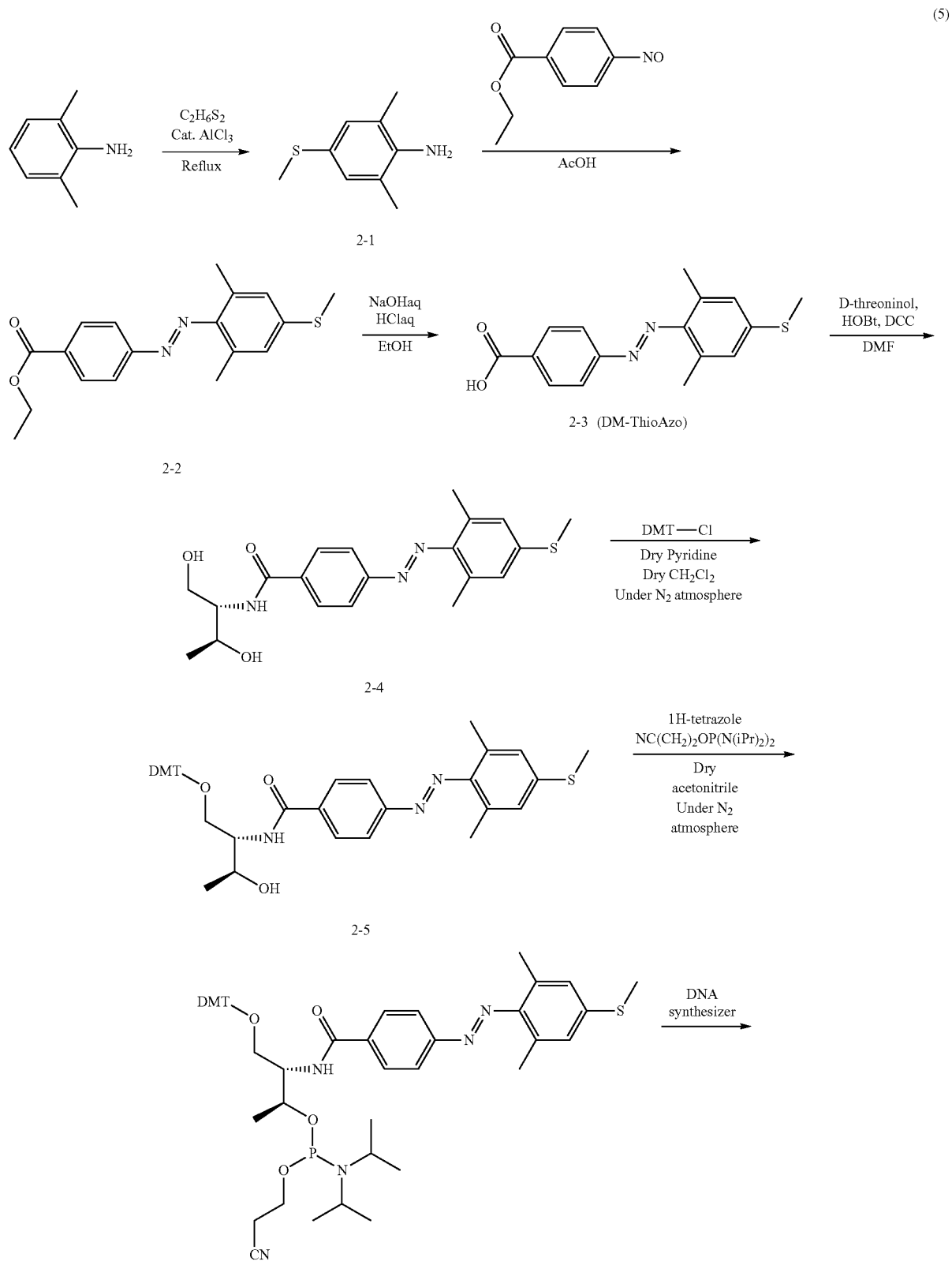
(5)

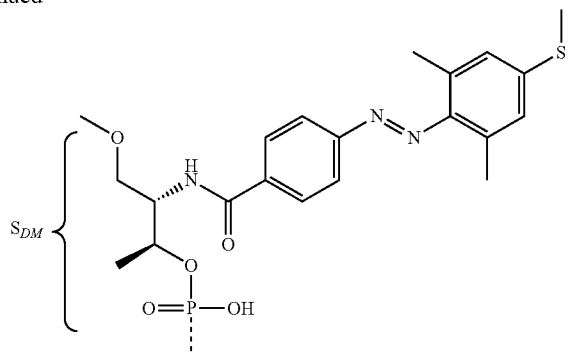

(Synthesis of Compound 2-1 (4-methylthio-2,6-dimethylaniline))

0.72 g (5.40 mmol) of crushed aluminum chloride (AlCl$_3$) and 9.84 g (0.081 mol) of 2,6-dimethylaniline were placed in a two-necked recovery flask, and refluxed for 30 minutes at 150° C. The resulting suspension was allowed to cool naturally to about 100° C., and 7.63 g of dimethyl disulfide was added and refluxed for 14 hours at 160° C. A 1 N aqueous solution of sodium hydrochloride was added to the mixture, which was then extracted one time with ethyl acetate, and then extracted two more times with ethyl acetate from the water phase. All the ethyl acetate solutions used in extraction were combined, and washed four times with saturated aqueous sodium chloride solution. The resulting organic layer was dried with magnesium sulfate and concentrated under reduced pressure, and the residue was purified by silica gel column chromatography (hexane:ethyl acetate=20:1 developing solvent) to obtain 6.72 g of a Compound 2-1. The yield was about 49.4%, as a mixture with unreacted raw materials.

(Synthesis of Compound 2-2)

1.08 g (6.03 mmol) of 4-nitrosobenzoic acid ethyl ester and 0.87 g (5.20 mmol) of Compound 2-1 were added to a recovery flask, dissolved in 30 mL of acetic acid, and reacted for 10 hours or more. After the reaction, the reaction solution was extracted one time with ethyl acetate, and the resulting organic layer was washed with saturated aqueous sodium bicarbonate solution, and then washed with saturated aqueous sodium chloride solution. The organic layer was dried with magnesium sulfate and then concentrated under reduced pressure, and the residue was purified by silica gel column chromatography (hexane:ethyl acetate=20:1 developing solvent) to obtain 1.14 g (3.47 mmol) of a Compound 2-2 with a yield of 66.7%.

(Synthesis of Compound 2-3)

1.14 g (3.47 mmol) of the Compound 2-2 was dissolved in 80 mL of ethanol in a recovery flask, and 0.26 g (4.45 mmol) of sodium hydroxide dissolved in 10 mL of distilled water was added and reacted for 10 hours or more. An aqueous hydrochloric acid solution was added to the reaction solution to make it acidic, and this was extracted one time with ethyl acetate to obtain an organic layer. The resulting organic layer was washed with saturated aqueous sodium chloride solution, and the organic layer was concentrated under reduced pressure to obtain 1.04 g (3.47 mol) of a Compound 2-3. The yield was about 100%.

(Synthesis of Compound 2-4)

1.04 g (3.47 mmol) of the Compound 2-3, 0.42 g (3.99 mmol) of D-threoninol and 0.58 g (4.29 mmol) of 1-hydroxybenzotriazol (HOBO were placed in a recovery flask, and dissolved in 20 mL of dimethylformamide (DMF). 0.89 g (4.31 mmol) of dicyclohexylcarbodiimide (DCC) dissolved in 10 mL of dimethylformamide were prepared, gradually added to the recovery flask, and reacted for 10 hours or more. Next, the reaction solution in the recovery flask was suction filtered, and the filtrate after removal of the solids was concentrated under reduced pressure to obtain a residue. The residue of the filtrate was purified by silica gel column chromatography (chloroform:methanol=20:1 developing solvent) to obtain 1.34 g (3.47 mmol) of a Compound 2-4. The yield was about 100%.

(Synthesis of Compound 2-5)

1.34 g (3.47 mmol) of the Compound 2-4 was placed in a two-necked recovery flask, and after substitution of nitrogen in the two-necked recovery flask, the compound was dissolved in 20 mL of dehydrated pyridine and immersed in an ice bath. A solution of 1.46 g (4.31 mmol) of dimethoxytrityl chloride (DMT-Cl) dissolved in 10 mL of dehydrated dichloromethane was prepared in a separate two-necked recovery flask, and this solution was gradually dripped into the other two-necked recovery flask containing the Compound 2-4. After completion of dripping the ice bath was removed, and the contents of the two-necked recovery flask were reacted for about 4 hours with the reaction monitored by thin-layer chromatography (TLC). The reaction solution was concentrated under reduced pressure and azeotroped three times with toluene, and the pyridine in the reaction solution was removed. The residue of the reaction solution was purified by silica gel column chromatography (hexane:ethyl acetate=1:1, triethylamine=3 vol % developing solvent) to obtain 1.41 g (2.04 mmol) of a Compound 2-5 with a yield of 58.8%.

(Synthesis of Compound 2-6)

0.14 g (0.20 mmol) of the Compound 2-5 was placed in a two-necked recovery flask, and following nitrogen substitution, was azeotroped two times with dehydrated acetonitrile. Next, 0.072 g (0.23 mmol) of an amiditing reagent (2-cyanoethyl N,N,N',N'-tetraisopropyl phosphoramidite) was added, and the mixture was further azeotroped one time with acetonitrile. This was then dissolved in 10 mL of acetonitrile, and cooled by immersion in an ice bath. 0.017 g (0.24 mmol) of 1H-tetrazole was taken in a separate two-necked flask, azeotroped two times with acetonitrile, and then dissolved in 5 mL of acetonitrile. The tetrazole solution was added slowly to the other flask, and reacted for about 4 hours. Next, the reaction solution was concentrated under reduced pressure, and the residue was purified by silica gel column chromatography (hexane:ethyl acetate=1:1, triethylamine=3 vol % developing solvent) to obtain 0.05 g (0.056 mmol) of a Compound 2-6. The yield was 28%.

(Oligonucleotide Synthesis)

The resulting Compound 2-6 was dissolved in 0.8 mL of acetonitrile, and used in oligonucleotide synthesis. Using the Compound 2-6 as an amidite monomer, an oligonucleotide was synthesized with a DNA synthesizer. The sequence of the synthesized oligonucleotide is shown below. SDM here indicates a residue containing the azobenzene derivative of Example 1 as shown in Formula (6) below. As comparative examples, oligonucleotides were prepared in which X=S (Comparative Example 1-1) and X=Z (Comparative Example 1-2) in 1a-X in the sequence below. S and Z are as shown in Formula (6) below. As shown below, moreover, a sequence 1b-0 complementary to 1a-X was also synthesized.

(SEQ ID NO: 1)
1a-X: 5'-GGTATCXGCAATC-3' (X = SDM, S, Z)
(SEQ ID NO: 2)
1b-0: 3'-CCATAGCGTTAG-5'

[C12]

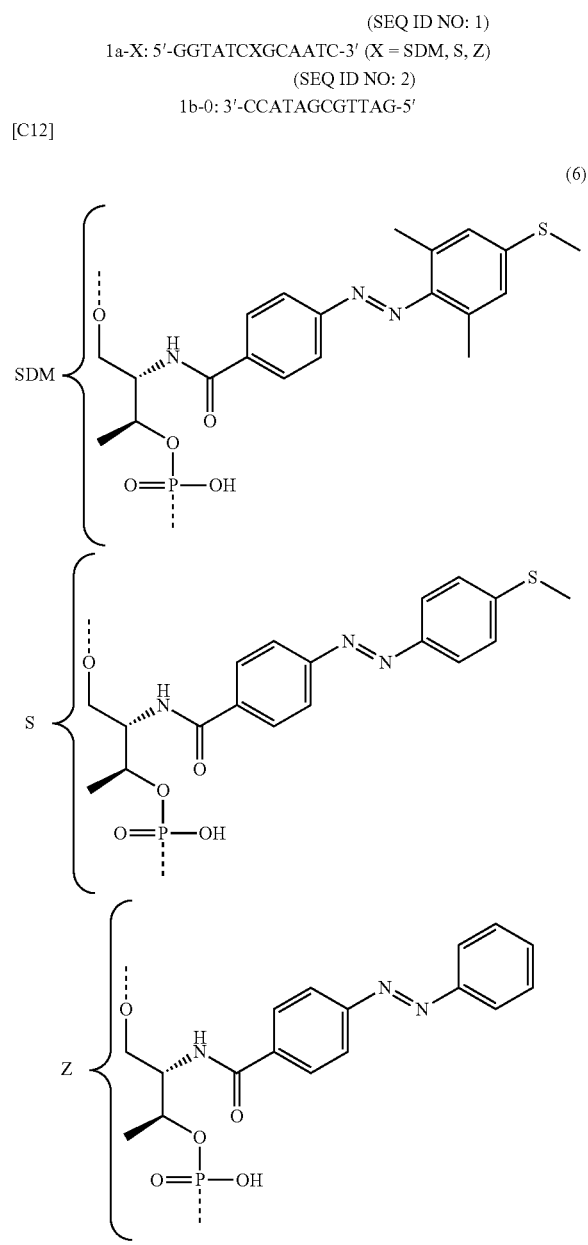

(6)

(Evaluation of Photo-control Ability)

FIG. 1 shows the absorption spectra of 1a-SDM (solid line: Example 1) and 1a-Z (broken line: Comparative Example 1-2) in ultraviolet-visible spectroscopy (UV-Vis). Measurement was performed under conditions of 1a-X concentration 20 μM, sodium chloride concentration 100 mM, pH 7.0 (10 mM, phosphate buffer). As shown in FIG. 1, the maximum absorption was near 400 nm in Example 1 but less than 350 nm in Comparative Example 1-2. These results show that the oligonucleotide of Example 1 can undergo trans-cis isomerization when irradiated with light having a wavelength in the visible light range of 400 nm or more, while the oligonucleotide of Comparative Example 1-2 required irradiation with light having a wavelength in the ultraviolet range of less than 400 nm in order to undergo a trans-cis isomerization reaction.

(Evaluation of Isomerization by Visible Light)

(UV-Vis Spectrum)

Next, the 1a-X sequences of Example 1, Comparative Example 1-1 and Comparative Example 1-2 were hybridized with the 1b-0 sequence, to obtain complexes having double strands designed with a wedge shape. The resulting complexes were irradiated with visible light, and isomerization from the stable trans-form to the unstable cis-form was evaluated. Isomerization in response to visible light was evaluated by maintaining the temperature of the solution containing each complex at 60° C., and irradiating each for 10 minutes with xenon lamp light passed through a 400 nm interference filter. Investigation of the absorption spectra of the complexes confirmed 60% or greater isomerization to the cis-form in Example 1 and Comparative Example 1-1. In Comparative Example 1-2, however, the isomerization rate to the cis-form was 15% or less. In the case of Comparative Example 1-2, the isomerization reaction was also investigated using light in the ultraviolet range, by irradiating for 5 minutes with xenon lamp light passed through a UVD-36C filter. As a result, 70% or greater isomerization to the cis-form was confirmed from the absorption spectrum.

Thus, the complexes (X=S, SDM) of the oligonucleotides of Example 1 and Comparative Example 1-1 underwent satisfactory trans-cis isomerization in response to irradiation with visible light at 400 nm. However, the complex (X=Z) of the oligonucleotide of Comparative Example 1-2 did not undergo satisfactory trans-cis isomerization in response to irradiation with visible light at 400 nm. These results correlate with the absorption spectra shown in FIG. 1.

In the case of Example 1, reverse isomerization from the cis-form to the trans-form in response to irradiation with light at 450 nm was also confirmed. Thus, the oligonucleotide of Example 1 is reversibly photoisomerized only by visible light irradiation.

(Evaluation of ΔTm)

The melting temperatures Tm of the complexes of Example 1, Comparative Example 1-1 and Comparative Example 1-2 were measured. The melting temperature Tm of the double strand of each oligonucleotide was determined from the temperature change of light absorbance of light with a wavelength of 260 nm using the methods described in Nature Protocols 2007, Vol. 2, pp. 203 to 212. The changes in melting temperature accompanying photo-isomerization of the double strand 1a-X/1b-0 are shown in Table 1 below. The measurement conditions were: oligonucleotide concentration 5 μM, sodium chloride concentration 100 mM, pH 7.0 (10 mM phosphate buffer). The melting temperature difference was calculated as ΔTm=(trans-form Tm)−(cis-form Tm). The results are shown in Table 1.

TABLE 1

| | | Melting Temperature Tm/° C. | | |
|---|---|---|---|---|
| | X | Trans-form | Cis-form | ΔTm/° C. |
| Example 1 | SDM | 48.3 | 34.9 | 13.4 |
| Comparative Ex. 1-1 | S | 46.1 | 45.2 | 0.9 |
| Comparative Ex. 1-2 | Z | 48.9 | 43.2 | 5.7 |

As shown in Table 1, a large ΔTm of 13.4° C. was observed from trans-cis isomerization even with a wedge-shaped complex design, far superior to the ΔTm values for Comparative Example 1-1 and Comparative Example 1-2. Thus, the complex of Example 1 was shown to isomerize into the cis-form in response to visible light at 400 nm, and to have superior photo-control ability.

(Thermal Isomerization Speed of Cis-form)

Next, the speed of thermal isomerization from the cis-from to the trans-form was measured in Example 1, Comparative Example 1-1 and Comparative Example 1-2. The thermal isomerization speeds were calculated by light irradiating a buffer solution (sodium chloride 100 mM, pH 7.0 (10 mM phosphate buffer)) of the single-stranded 1a-X to isomerize it to the cis-form, maintaining it at 60° C. while measuring the absorption spectrum periodically, and calculating the rate of increase in absorption corresponding to the maximum absorption wavelength of the trans-form. Light irradiation was performed for 10 minutes using xenon lamp light passed through a 400 nm interference filter for Example 1 and Comparative Example 1-1, and for 5 minutes using xenon lamp light passed through a UVD-36C filter for Comparative Example 1-2. Table 2 shows cis-trans thermal isomerization rates. The 1a-X (X=SDM, Z, S) concentration was 20 μM, and the measurement temperature was 60° C.

TABLE 2

| | Sequence | Half-life/h | Thermal isomerization speed constant/h$^{-1}$ |
|---|---|---|---|
| Example 1 | 1a-SDM | 6.4 | 0.11 |
| Comparative Example 1-1 | 1a-S | 0.36 | 1.9 |
| Comparative Example 1-2 | 1a-Z | 3.3 | 0.21 |

The thermal isomerization rate needs to be slow for purposes of hybridization control using light. In general, thermal isomerization of the cis-form is accelerated by introducing an electron-releasing group into the para position of the azo group of azobenzene. As shown in Table 2, with the 1a-S of Comparative Example 1-1, which has an azobenzene with an introduced methylthio group in the para position of the azo group, the cis-trans thermal isomerization rate is about 10 times faster than with the 1a-Z of Comparative Example 1-2, which has an unsubstituted azobenzene. Thus, chemical modification in the para position of the azo group generally has the effect of thermally destabilizing the cis-form. However, with the 1a-SDM of Example 1, thermal stability of the cis-form was improved and the thermal isomerization rate was even slower than that of the unsubstituted azobenzene (1a-Z) despite the presence of a methylthio group in the para position of the azo group.

As discussed above, with an oligonucleotide having the novel alkylthioazobenzene of Example 1 it is possible to control the isomerization rates of the structural isomers by irradiation with light having a wavelength in the visible light range. More specifically, it is possible to provide an oligonucleotide whereby isomerization of structural isomers can be achieved by irradiation with light having a wavelength in the visible light range, and having a large melting temperature difference ΔTm of the structural isomers. Moreover, the thermal isomerization properties of the cis-form are favorably, and hybridization can be controlled satisfactorily using visible light.

Example 2

In Example 2, an oligonucleotide represented by Formula (3a) below containing isopropylthioazobenzene is explained as an example of the oligonucleotide represented by Formula (3) above.

[C13]

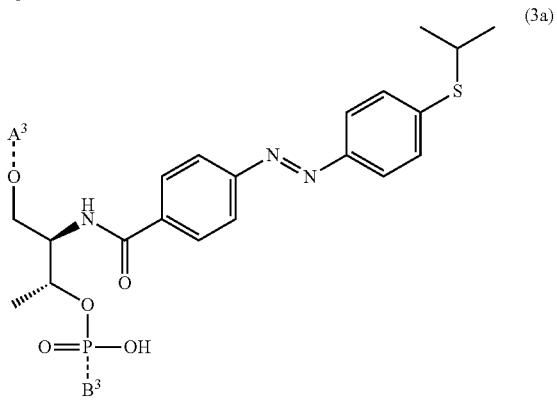

(3a)

(Synthesis of Oligonucleotide Containing Isopropylthioazobenzene)

The oligonucleotide containing isopropylthioazobenzene shown in Formula (3a) below was synthesized in accordance with the scheme of Formula (7) below. The Compounds 3-1-1 to 3-1-6 used in synthesis are shown in Formula (7) below. Compounds 3-1-2 to 3-1-6 constitute one example of the azobenzene derivative of Formula (14) above.

[C14]

(7)

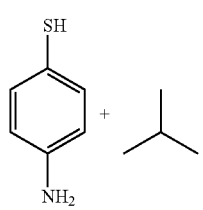 + 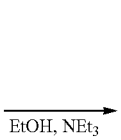 $\xrightarrow{\text{EtOH, NEt}_3}$ 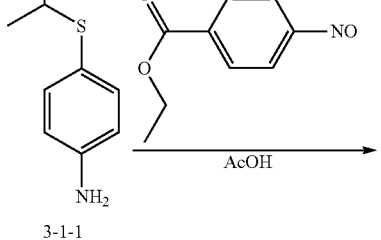 $\xrightarrow{\text{AcOH}}$ 3-1-1

-continued
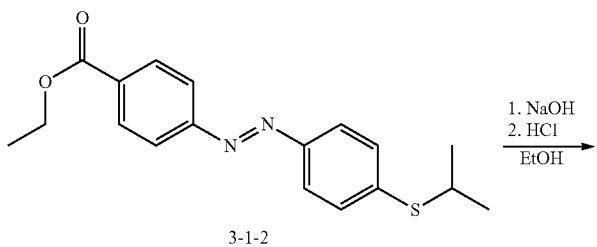
3-1-2
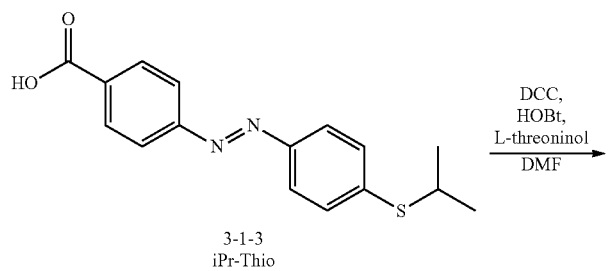
3-1-3
iPr-Thio
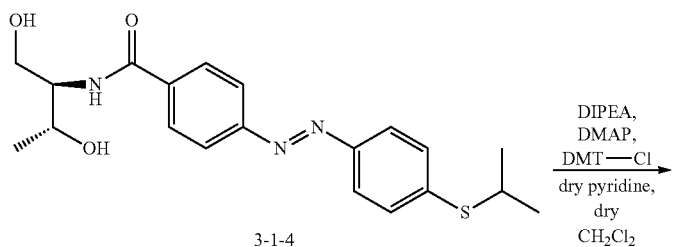
3-1-4
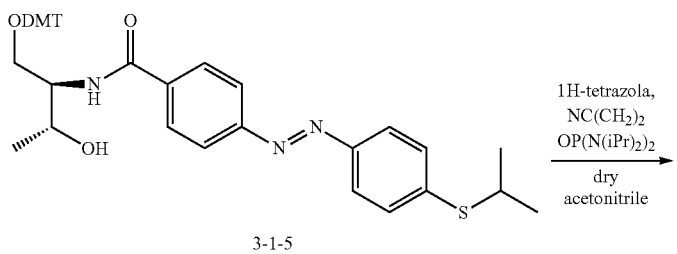
3-1-5
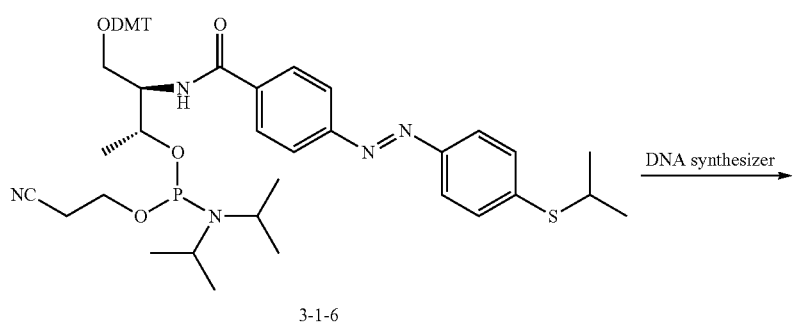
3-1-6

-continued

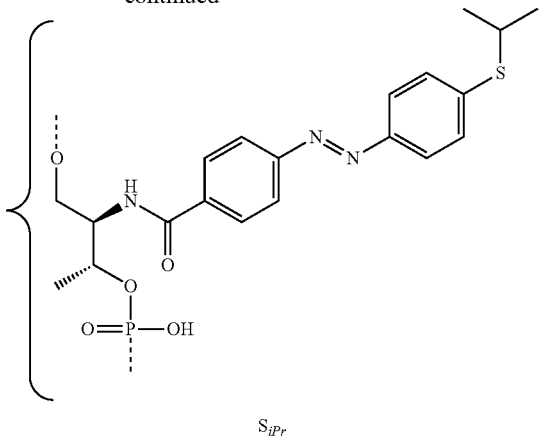

$S_{iPr}$ (Synthesis of Compound 3-1-1)

0.4 g (3.19 mmol) of 4-aminobenzenethiol was taken and dissolved in about 20 mL of ethanol, and 8 mL of triethylamine were added. 0.38 mL (1.2 eq.) of 2-iodopropane were dripped in, and reacted for about 7 hours. This was then suction filtered, concentrated under reduced pressure, vacuum dried, and then purified by silica gel column chromatography (hexane:ethyl acetate=3:1, triethylamine=3 vol % developing solvent) to obtain a Compound 3-1-1. 0.22 g (1.32 mmol) was obtained, with a yield of 41.4%.

(Synthesis of Compound 3-1-2)

0.22 g of the Compound 3-1-1 and 0.32 g (1.2 eq.) of ethyl-p-nitrosobenzoate were dissolved in an acetic acid solution, and reacted at room temperature for about 3 hours. The progress of the reaction was confirmed by thin-layer chromatography (TLC). After the reaction, the solution was concentrated under reduced pressure to reduce the liquid volume, extracted with ethyl acetate, and separated one time with distilled water, three times with saturated aqueous sodium bicarbonate solution, and two times with saturated aqueous sodium chloride solution. The organic layer was then dried with magnesium sulfate, filtered, concentrated under reduced pressure, vacuum dried, and purified by silica gel column chromatography (hexane:ethyl acetate 12:1 developing solvent) to obtain a Compound 3-1-2. 0.5 g (1.52 mmol) was obtained, with a yield of about 100%.

(Synthesis of Compound 3-1-3)

0.5 g of the Compound 3-1-2 were dissolved in ethanol, and 3.8 mL (5 eq.) of 2 N sodium hydroxide was added and agitated overnight. 1 N hydrochloric acid was added to make the mixture acidic, and the reaction was confirmed by thin-layer chromatography, after which the solution was concentrated under reduced pressure, extracted with ethyl acetate, and separated (one time with distilled water, two times with sodium chloride). The organic layer was dried with magnesium sulfate, filtered, concentrated under reduced pressure, and vacuum dried to obtain a Compound 3-1-3. 0.41 g (1.36 mmol) was obtained, with a yield of 89.8%.

(Synthesis of Compound 3-1-4)

0.34 g of the Compound 3-1-3, 0.14 g (1.2 eq.) of L-threoninol and 0.18 g (1.2 eq.) of 1-hydroxybenzotriazole (HOBt) were taken in a flask, and dissolved in dimethylformamide (DMF). Next, 0.28 g (1.36 mmol) of dicyclohexyl carbodiimide was taken in a beaker, and dissolved in dimethyl fumarate. The solution of dissolved dicyclohexyl carbodiimide was dripped slowly into the flask, and reacted overnight. The solids were removed by filtration, and the filtrate was concentrated under reduced pressure, vacuum dried, and purified by silica gel column chromatography (chloroform:methanol=9:1 developing solvent) to obtain a Compound 3-1-4. 0.50 g (1.29 mmol) was obtained, with a yield of about 100%.

(Synthesis of Compound 3-1-5)

The Compound 3-1-4 (0.5 g) was placed in a two-necked flask, nitrogen substituted, and dissolved in dehydrated pyridine. 0.26 mL (1.2 eq.) of N,N-diisopropylethylamine (DIPEA) was then added. 0.50 g (1.2 eq.) of dimethoxytrityl chloride (DMT-Cl) and 0.03 g (1.2 eq.) of N,N-dimethyl-4-aminopyridine (DMAP) were placed in a separate flask, nitrogen substituted, and dissolved in dehydrated dichloromethane. The solution in the flask with the dissolved dimethoxytrityl chloride was dripped slowly into the solution in the two-necked flask with the Compound 3-1-4 in an ice bath, and reacted as is for 2 hours in the ice bath. The progress of the reaction was confirmed by thin-layer chromatography, and the mixture was azeotroped two times with toluene and then vacuum dried and purified by silica gel column chromatography (hexane:ethyl acetate 1:1, triethylamine=3 vol % developing solvent) to obtain a Compound 3-1-5. 0.52 g (0.75 mmol) was obtained, with a yield of 58.4%.

(Synthesis of Compound 3-1-6)

0.28 g of the Compound 3-1-5 were placed in a two-necked flask, nitrogen substituted, dissolved in a suitable amount of dehydrated acetonitrile, and azeotroped two times. 0.16 mL of an amiditing reagent (2-cyanoethyl N,N,N',N'-tetraisopropyl phosphoramidite) was added with a syringe to the mixture, which was then azeotroped two times with dehydrated acetonitrile. This was then dissolved in a suitable amount of dehydrated acetonitrile. 0.034 g (0.49 mmol) of 1H-tetrazole were then placed in a separated pear-shaped flask, nitrogen substituted, azeotroped two times with dehydrated acetonitrile, and then dissolved in dehydrated acetonitrile. Tetrazole was dripped in slowly in an ice bath, and the mixture was reacted for 1 hour. This was then separated two times with a saturated aqueous sodium bicarbonate solution and three times with a saturated aqueous sodium chloride solution, dried with magnesium sulfate, filtered, concentrated under reduced pressure, and vacuum dried to obtain a Compound 3-1-6. The yield was about 100%.

The Compound 3-1-6 is an amidite monomer. An oligonucleotide containing the isopropylthioazobenzene residue (SiPr) shown in Formula (7) above was synthesized using the Compound 3-1-6 with a DNA synthesizer.

Comparative Example 2-1

(Synthesis of Oligonucleotide Containing Isobutylthioazobenzene)

An oligonucleotide containing isobutylthioazobenzene was synthesized in accordance with the scheme of Formula (8) below as Comparative Example 2-1. The Compounds 3-2-1 to 3-2-6 used in synthesis are shown in Formula (8) below.

[C15]

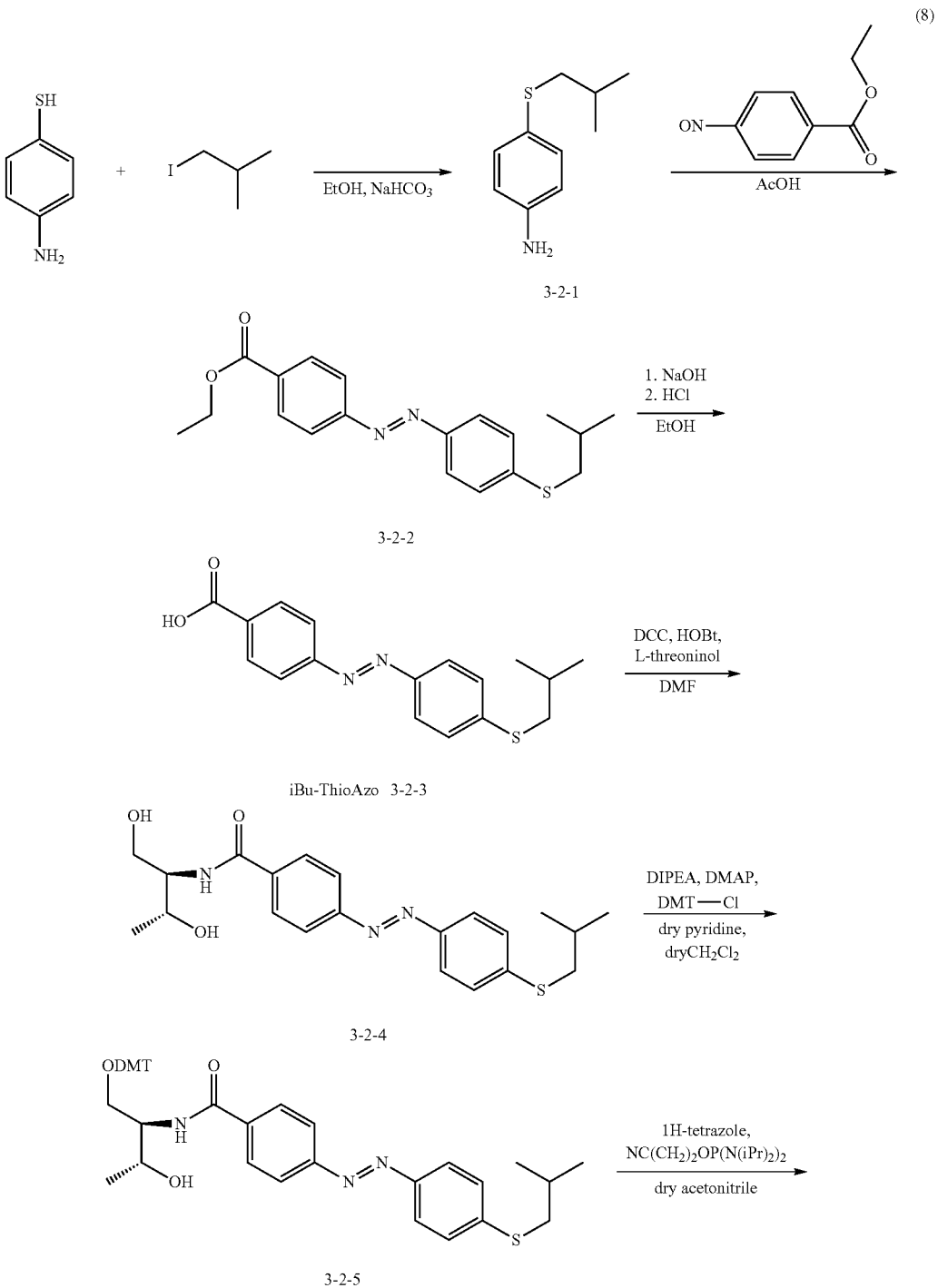

-continued

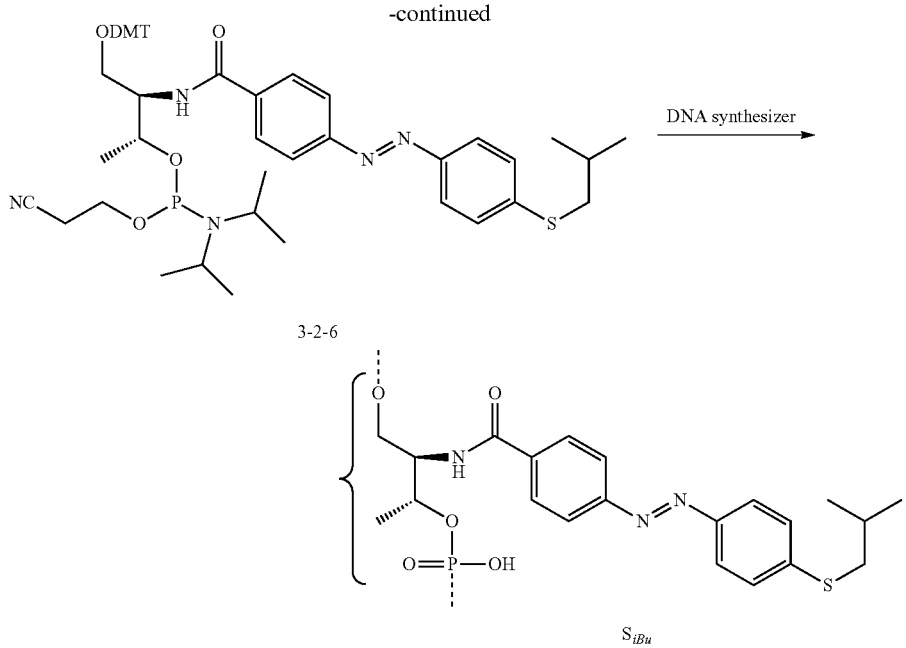

(Synthesis of Compound 3-2-1)

1.0 g of 4-aminobenzenethiol was dissolved in ethanol, and the solution was made basic (pH=8) by addition of aqueous sodium carbonate solution, and reacted overnight with agitation. After the reaction, this was concentrated under reduced pressure to reduce the amount of liquid, extracted with ethyl acetate, and washed three times with saturated aqueous sodium bicarbonate solution and two times with saturated aqueous sodium chloride solution. The organic layer was then dried with magnesium sulfate, filtered, concentrated under reduced pressure, and vacuum dried. This was purified by silica gel column chromatography (hexane:ethyl acetate=1:1, triethylamine=3 vol % developing solvent) to obtain a Compound 3-2-1. 0.35 g (1.93 mmol) was obtained, with a yield of 24.2%.

(Synthesis of Compound 3-2-2)

0.22 g of the Compound 3-2-1 and 0.26 g (1.2 eq.) of ethyl-p-nitrosobenzoate were dissolved in acetic acid solution, and reacted for about 20 hours. This was extracted with ethyl acetate and washed one time with distilled water, four times with saturated aqueous sodium bicarbonate solution, and three times with saturated aqueous sodium chloride solution. The organic layer was then dried with magnesium sulfate, filtered, concentrated under reduced pressure, and vacuum dried. This was purified by silica gel column chromatography (hexane:ethyl acetate=14:1 developing solvent) to obtain a Compound 3-2-2. 0.38 g (1.11 mmol) was obtained, with a yield of 91.7%.

(Synthesis of Compound 3-2-3)

0.38 g of the Compound 3-2-2 was dissolved in about 10 mL of ethanol, and 5 mL of 2 N sodium hydroxide was added and reacted overnight. After the reaction hydrochloric acid was added, giving a pH of 7 or less, and the solution was extracted with ethyl acetate and washed one time with distilled water and two times with saturated aqueous sodium chloride solution. The organic layer was then dried with magnesium sulfate, concentrated under reduced pressure, and vacuum dried to obtain a Compound 3-2-3. 0.36 g (1.14 mmol) was obtained, with a yield of about 100%.

(Synthesis of Compound 3-2-4)

0.36 g of the Compound 3-2-3, 0.12 g of L-threoninol and 0.18 g of 1-hydroxybenzotriazole (HOBt) were dissolved in dimethylformamide (DMF). 0.28 g of dicyclohexyl carbodiimide was dissolved in dimethylformamide in a separate flask, and this was added little by little to the first flask, and reacted overnight. The precipitated solids were then filtered out, concentrated under reduced pressure, and vacuum dried. This was purified by silica gel column chromatography (developing solvent changed continuously from chloroform:methanol=40:1 to 10:1 according to the progress of analysis using the gradient method) to obtain a Compound 3-2-4. 0.39 g (0.97 mmol) was obtained, with a yield of 85.2%.

(Synthesis of Compound 3-2-5)

0.39 g of the Compound 3-2-4 was taken in a two-necked flask, nitrogen substituted, and dissolved in 8 mL of dehydrated pyridine. 0.19 mL of N,N-diisopropylethylamine (DIPEA) was added to this. 0.40 g of dimethoxytrityl chloride and 0.023 g of N,N-dimethyl-4-aminopyridine (DMAP) were taken in a separate two-necked flask, nitrogen substituted, and dissolved by addition of 4 mL of dehydrated dichloromethane. After both had dissolved, the two-necked flask containing the Compound 3-2-4 and the two-necked flask containing the dimethoxytrityl chloride were connected by a fine wire-shaped tube, and the solution containing the dimethoxytrityl chloride was dripped slowly into the two-necked flask containing the Compound 3-2-4 in an ice bath, and reacted for about 3 hours. After the reaction, this was extracted with ethyl acetate, and washed one time with distilled water, three times with saturated aqueous sodium bicarbonate solution, and two times with saturated aqueous sodium chloride solution. The organic layer was then dried with magnesium sulfate, filtered, concentrated under reduced pressure, vacuum dried, and purified by silica gel column chromatography (developing solvent changed continuously from hexane:ethyl acetate:triethylamine=200:100:9 to 50:50:3 according to the progress of analysis using the gradient method) [to obtain a Compound 3-2-5]. 0.44 g (0.63 mmol) was obtained, with a yield of 64.4%.

(Synthesis of Compound 3-2-6)

0.24 g (0.34 mmol) of the Compound 3-2-5 was placed in a two-necked flask i, and nitrogen substituted. A suitable amount of dehydrated acetonitrile was added to mixture, which was then azeotroped two times, after which 1 mL of an amiditing reagent (2-cyanoethyl N,N,N',N'-tetraisopropyl phosphoramidite) was added, and the mixture was further azeotroped with dehydrated acetonitrile and dissolved in dehydrated acetonitrile. 0.29 g (0.41 mmol) of 1H-tetrazole was placed in a separated flask ii, nitrogen substituted, azeotroped two times with dehydrated acetonitrile, and then dissolved in dehydrated acetonitrile. Flask ii was gradually dripped into flask i in an ice bath, the ice bath was removed, and the mixture was reacted for about 1 hour. This was confirmed by thin-layer chromatography, concentrated under reduced pressure, vacuum dried, and purified by silica gel column chromatography (hexane:ethyl acetate=2:1, triethylamine 3 vol % developing solvent) to obtain a Compound 3-2-6. The yield was about 100%.

The Compound 3-2-6 is an amidite monomer. An oligonucleotide containing the isobutylthioazobenzene residue (SiBu) shown in Formula (8) above was synthesized using the Compound 3-2-6 with a DNA synthesizer.

Comparative Example 2-2

Synthesis of Oligonucleotide Containing Tert-Butylthioazobenzene

An oligonucleotide containing tert-butylthioazobenzene was synthesized in accordance with the scheme of Formula (9) below as Comparative Example 2-2. The Compounds 3-3-1 to 3-3-6 used in synthesis are shown in Formula (9) below.

[C16]

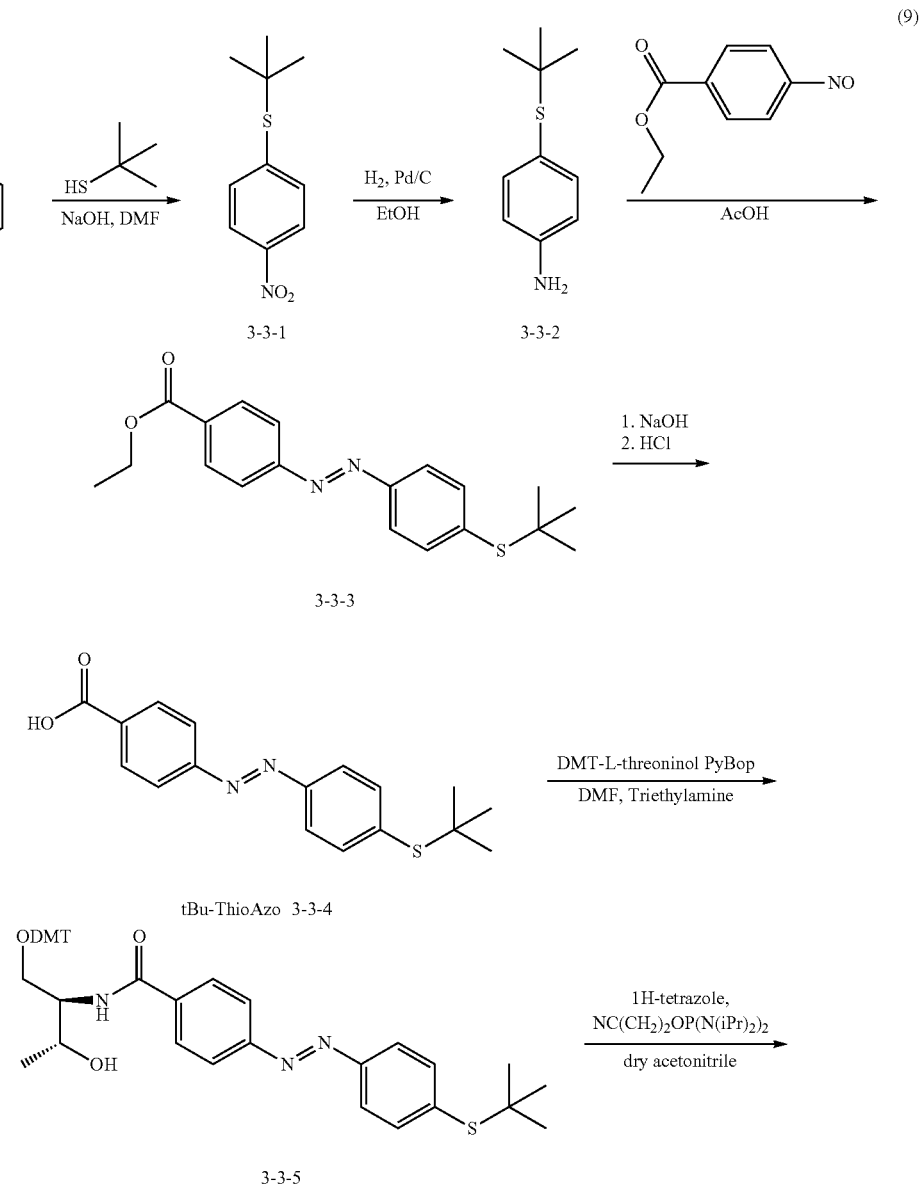

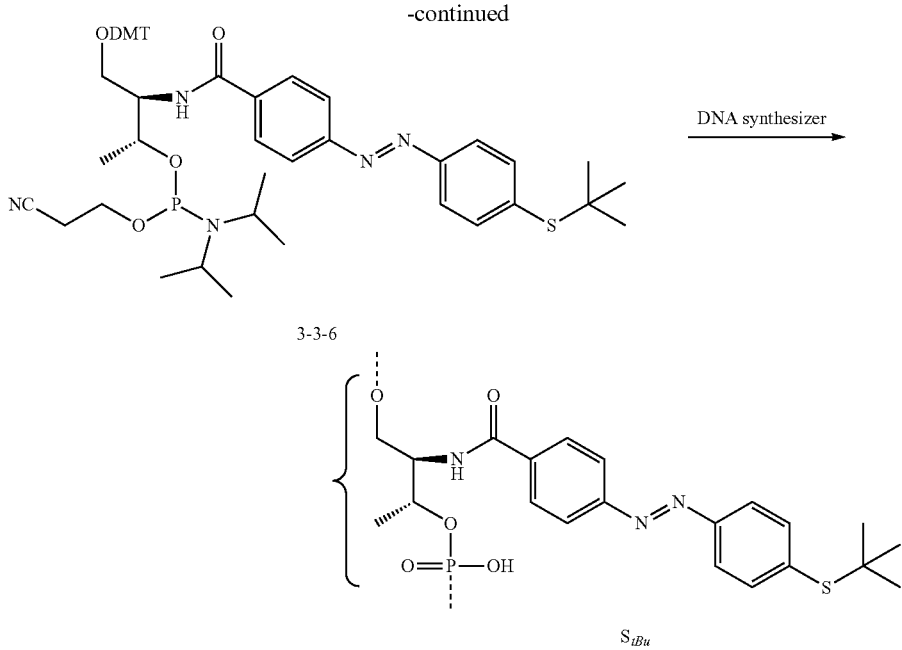

3-3-6

(Synthesis of Compound 3-3-1)

0.1 g of sodium hydroxide (solid) was placed in a flask, and nitrogen substituted. This was dissolved in dehydrated dimethylformamide, 0.17 mL of 2-methyl-2-propanethiol was added and agitated until the sodium hydroxide dissolved, and 0.17 mL of 4-fluoronitrobenzene was then added and reacted overnight. This was transferred to a separation funnel, extracted with ethyl acetate, and washed one time with distilled water, three times with saturated aqueous sodium bicarbonate solution and three times with saturated aqueous sodium chloride solution using the separation funnel. The organic layer was then dried with magnesium sulfate, concentrated under reduced pressure, and vacuum dried. This was then purified by silica gel column chromatography (hexane:ethyl acetate 20:1 developing solvent) to obtain a Compound 3-3-1. 0.33 g (1.56 mmol) was obtained, with a yield of about 100%.

(Synthesis of Compound 3-3-2)

0.33 g of the Compound 3-3-1 was dissolved in ethanol, and a suitable amount of palladium on carbon (Pd/C) was added. Next, the reaction system was hydrogen substituted with hydrogen filling a nitrogen balloon, and agitated vigorously overnight. The palladium on carbon was then removed by filtration, and the mixture was concentrated under reduced pressure, vacuum dried, and then purified by silica gel chromatography (hexane:ethyl acetate=10:1 developing solvent) to obtain a Compound 3-3-2. 0.21 g (1.16 mmol) was obtained, with a yield of 74.2%.

(Synthesis of Compound 3-3-3)

0.21 g of the Compound 3-3-2 and 0.25 g of ethyl-p-nitrosobenzoate were dissolved in glacial acetic acid, and reacted for about 2 hours. The progress of the reaction was confirmed by thin-layer chromatography, and the mixture was dissolved in ethyl acetate, and washed four times with saturated aqueous sodium bicarbonate solution and one time with saturated aqueous sodium chloride solution, using a separation funnel. This was then dried with magnesium sulfate, concentrated under reduced pressure, vacuum dried, and purified by silica gel column chromatography (hexane:ethyl acetate=20:1 developing solvent) to obtain a Compound 3-3-3. 0.40 g (1.17 mmol) was obtained, with a yield of 73.9%.

(Compound 3-3-4)

0.40 g of the Compound 3-3-3 was dissolved in ethanol, and 3.5 mL (5 eq.) of 2 N sodium hydroxide were added and reacted overnight. The progress of the reaction was confirmed by thin-layer chromatography, hydrochloric acid was added to make the pH acidic, the mixture was then dissolved in ethyl acetate and washed two times with saturated aqueous sodium chloride solution using a separation funnel, and the resulting organic layer was dried by addition of magnesium sulfate, concentrated under reduced pressure, and vacuum dried to obtain a Compound 3-3-4. 0.40 g (1.27 mmol) was obtained, with a yield of about 100%.

(Compound 3-3-5)

0.40 g of the Compound 3-3-4 was dissolved in dimethylformamide, and 0.66 g of (benzotriazole-1-yl-oxy)tripyrrolidinophosphonium hexafluorophosphate (PyBOP™) was added and agitated for 20 minutes. Dimethyl fumarate and 0.41 g (1 eq.) of 4,4'-dimethoxytrityl(DMT)-L-threoninol dissolved in triethylamine were added, and reacted overnight. The progress of the reaction was confirmed by thin-layer chromatography, and the mixture was concentrated under reduced pressure, vacuum dried, and purified by silica gel column chromatography to obtain a Compound 3-3-5. (The developing solvent was hexane:ethyl acetate 3:2, triethylamine=3 vol %). DMT-L-threoninol was synthesized by the methods described in Angewandte Chemie International Edition 2010, Vol. 49, pp. 5502 to 5506. 0.17 g (0.24 mmol) was obtained, with a yield of 18.9%.

(Compound 3-3-6)

0.17 g of the Compound 3-3-5 was placed in a two-necked flask, nitrogen substituted, and washed two times with a suitable amount of dehydrated acetonitrile. After addition of 0.09 mL of an amiditing reagent (2-cyanoethyl N,N,N'N'-tetraisopropyl phosphoramidite), this was dissolved in dehydrated acetonitrile. 0.02 g of 1H-tetrazole was also placed in a pear-shaped flask, nitrogen substituted in the same way, azeotroped two times with a suitable amount of dehydrated acetonitrile, and dissolved in dehydrated acetonitrile. The two-necked flask and the pear-shaped flask were connected with a fine wire-shaped tube, and the contents of the pear-shaped flask were dripped slowly into the two-necked flask in an ice bath. The ice bath was removed, and the reaction continued for about 1 hour. The progress of the reaction was confirmed by thin-layer chromatography, and the mixture was concentrated under reduced pressure and then extracted with ethyl acetate and washed one time with distilled water, two times with a saturated aqueous sodium bicarbonate solution, and two times with a saturated aqueous sodium chloride solution using a separation funnel. This was then dried by addition of magnesium sulfate, concentrated under reduced pressure, vacuum dried, and azeotroped again with dehydrated acetonitrile to obtain a Compound 3-3-6. The yield was about 100%.

This Compound 3-3-6 is an amidite monomer. An oligonucleotide containing the tert-butyl azobenzene residue (StBu) shown in Formula (9) above was synthesized using the Compound 3-3-6 with a DNA synthesizer.

The synthesized sequences are shown below.

```
                                           (SEQ ID NO: 1)
1a-X:5'-GGTATCXGCAATC-3' (X = SiPr, SiBu, StBu)

(SEQ ID NO: 2)
1b-0:3'-CCATAGCGTTAG-5'
```

(Evaluation of Photo-control Ability)
(UV-Vis spectrum)

Figure 2:
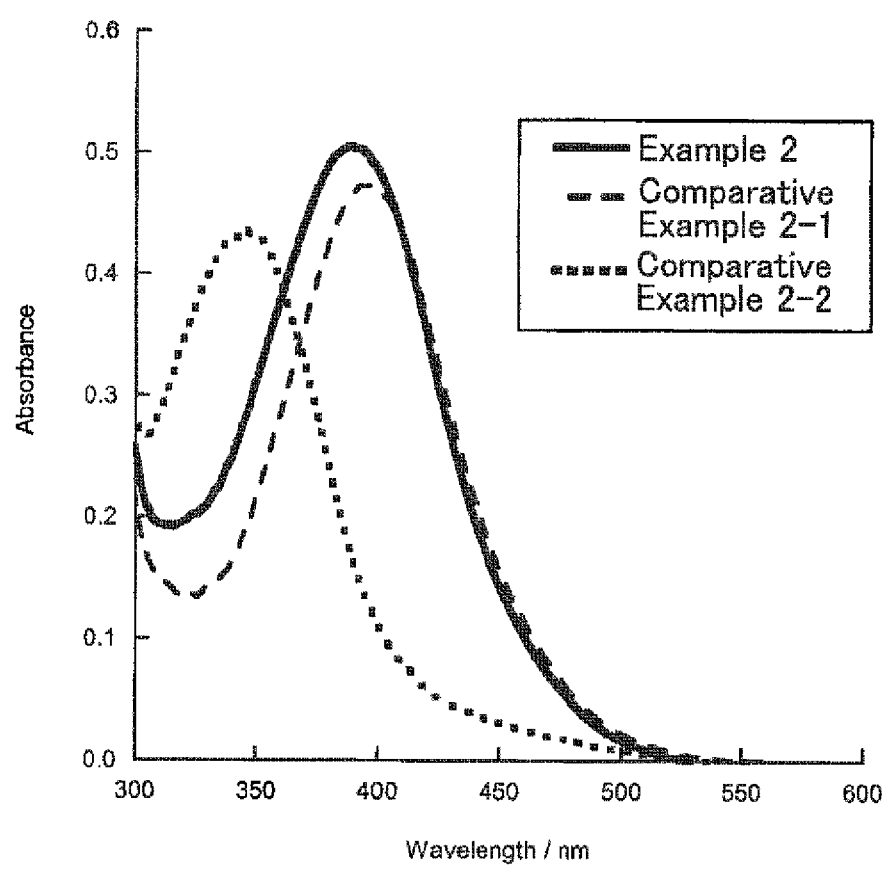
FIG. 2 shows ultraviolet and visible light absorption spectra of Example 2.

The absorption spectrum measurement results using UV-Vis are shown in FIG. 2 for the single-stranded forms of 1a-iPr (Example 2), 1a-iBu (Comparative Example 2-1) and 1a-tBu (Comparative Example 2-2). Measurement here was performed under conditions of 1a-X concentration 20 μM, sodium chloride concentration 100 mM, pH 7.0 (10 mM phosphate buffer).

As shown in FIG. 2, maximum absorption was obtained near 400 nm with the 1a-iPr of Example 2 and the 1a-iBu of Comparative Example 2-2. With the 1a-tBu of Comparative Example 2-2, on the other hand, the maximum absorption wavelength was not increased, and maximum absorption was obtained near 350 nm. The three-dimensional structures of the azobenzene derivatives of Example 2 and Comparative Example 2-2 were investigated by quantum chemical calculation (Gaussian09W). As a result, it was found that while in the Compound 3-3-4 of Comparative Example 2-2 the bond connecting the tert-butyl group (tBu group) with the sulfur atom (S) projects in a direction perpendicular to the benzene ring, in the Compound 3-1-3 of Example 2 the bond connecting the isopropyl group (iPr group) and the sulfur atom (S) projects within the same plane as the benzene ring. The results of quantum chemical calculation show that in Compound 3-3-4 steric hindrance with the hydrogen atoms of the benzene ring occurs because the tBu group is bulky, so that the bond connecting the tBu group and the sulfur atom is not located on the same flat plane as the benzene ring, thereby changing the electron arrangement of the sulfur atoms. It is thought that this is the reason why the electron releasing effect is weak and the absorption wavelength is shorter in the Compound 3-3-4 of the Comparative Example 2-2. In the Compound 3-1-3 of Example 2, on the other hand, there is no steric hindrance because the iPr group is not as bulky as the tBu group, and the bond connecting the iPr group and the sulfur atom is therefore located on the same plane as the benzene ring. It is thought that this is why a longer maximum absorption wavelength is obtained due to the satisfactory electron releasing effect in the Compound 3-1-3.

(Evaluation of ΔTm)

The melting temperatures Tm of the 1a-X/1b-0 double strands were measured next. In the case of X=iPr (Example 2) and iBu (Comparative Example 2-1), trans-cis isomerization was performed by irradiation for 10 minutes with xenon lamp light passed through a 400 nm interference filter, with the temperature of the solution maintained at 60° C. Isomerization of 60% or more into the cis-form by this operation was confirmed from the absorption spectrum. In the case of X=tBu (Comparative Example 2-2), irradiation was performed for 5 minutes with xenon lamp light passed through a 370 nm interference filter. Table 3 shows melting temperatures accompanying photo-isomerization of the 1a-X/1b-9 double strand. Measurement was performed under conditions of oligonucleotide concentration 5 μM, sodium chloride concentration 100 mM, pH 7.0 (10 mM phosphate buffer). The results are shown in Table 3. In Example 2, Comparative Example 2-1 and Comparative Example 2-2, the ΔTm values are negative because the cis-isomer is more stable than the trans-isomer.

TABLE 3

| | Melting temperature Tm/° C. | | |
|---|---|---|---|
| X | Trans-form | Cis-form | ΔTm/° C. |
| Example 2 | SiPr | 42.5 | 47.0 | −4.5 |
| Comparative Example 2-1 | SiBu | 44.5 | 46.4 | −1.9 |
| Comparative Example 2-2 | StBu | 40.5 | 46.8 | −6.3 |

As shown in Table 3, the absolute value of ΔTm was large and the photo-control ability was high in the system of Example 2 using an oligonucleotide having isopropylthioazobenzene. By contrast, in the system of Comparative Example 2-1 using an oligonucleotide having isobutylthioazobenzene, the absolute value of ΔTm was small, and the photo-control ability was insufficient. In the system of Comparative Example 2-2 using an oligonucleotide having tert-butylthioazobenzene, meanwhile, the absolute value of ΔTm was higher than the Tm of Example 2, but as shown in FIG. 2 the maximum absorption wavelength was 350 nm, which is in the ultraviolet range.

As discussed above, with the oligonucleotide of Example 2 having isopropylthioazobenzene, the isomerization reaction of structural isomers can be controlled by irradiation with light at a wavelength in the visible light range. More specifically, it is possible to provide an oligonucleotide having a large absolute value of the melting temperature difference ΔTm between structural isomers, whereby structural isomers can be isomerized by irradiation with light having a wavelength in the visible light range.

Example 3

In Example 3, a pair of oligonucleotides each containing a methylthioazobenzene as shown in Formula (4a) below are explained as an example of the oligonucleotide represented by Formula (4) above.

[C17]

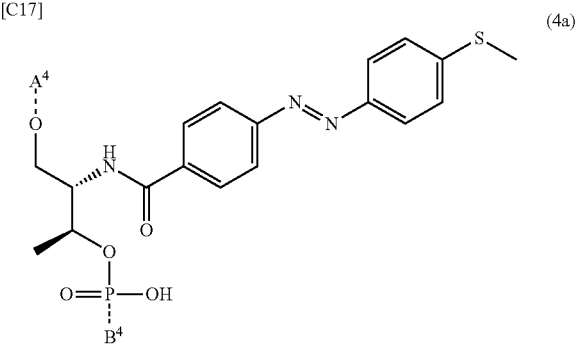
(4a)

A phosphoramidite monomer corresponding to Formula (4a) above was synthesized by the methods described in Chemistry A European Journal 2009, Vol. 15, pp. 10092 to 10102, and introduced into an oligonucleotide by the methods described in that journal. As described in that journal, moreover, the maximum absorption wavelength (maximum absorption wavelength of the UV-Vis absorption spectrum) of the residue containing the azobenzene derivative in the oligonucleotide shown in Formula (4a) above was 398 nm in aqueous solution.

The actual synthesized sequences are shown below. In the sequences below, "S" represents a residue containing the methylthiobenzene of Formula (4a) above. Oligonucleotide sequences 1a-S and 1b-S contain one S residue containing a methylthiobenzene. Sequences A4S and B4S contain four S residues.

```
1a-0:    5'-GGTATCGCAATC-3'    (SEQ ID NO: 3)
1a-S:    5'-GGTATCSGCAATC-3'   (SEQ ID NO: 1)
1b-0:    3'-CCATAGCGTTAG-5'    (SEQ ID NO: 2)
1b-S:    3'-CCATAGSCGTTAG-5'   (SEQ ID NO: 4)
A4S:     5'-CGSTTSAGSTTSCA-3'  (SEQ ID NO: 5)
B4S:     3'-GCSAASTCSAASGT-5'  (SEQ ID NO: 6)
```

(Evaluation of ΔTm)

The double strand melting temperature Tm of each oligonucleotide pair was determined from changes in absorbance at 260 nm, using the methods described in Nature Protocols 2007, Vol. 2, pp. 203 to 212. Isomerization into the cis-form was performed by irradiation for 15 minutes with xenon lamp light passed through a 400 nm interference filter, with the temperature of the solution maintained at 60° C. Isomerization of 60% or more of the cis-form by this operation was confirmed from the absorption spectrum. Table 4 shows the melting temperatures Tm of the double-stranded oligonucleotides with various introduced azobenzenes. Measurement was performed under conditions of sodium chloride concentration 100 mM, pH 7.0 (10 mM phosphate buffer).

TABLE 4

| | Oligonucleotide pair | Association mode | Concentration | Melting temp. Tm/° C. | | ΔTm/° C. |
| | | | | Trans-form | Cis-form | |
|---|---|---|---|---|---|---|
| Example 3-1 | 1a-S/1b-S | Associative | 5 μM | 52.4 | 43.1 | 9.3 |
| Example 3-2 | A4S/B4S | Associative | 2 μM | 54.0 | ≤0 | ≥54 |
| Comparative Example 3-1 | 1a-0/1b-0 | | 5 μM | 47.7 | | — |
| Comparative Example 3-2 | 1a-S/1b-0 | Wedge-shaped | 5 μM | 46.1 | 45.2 | 0.9 |

Figure 4:
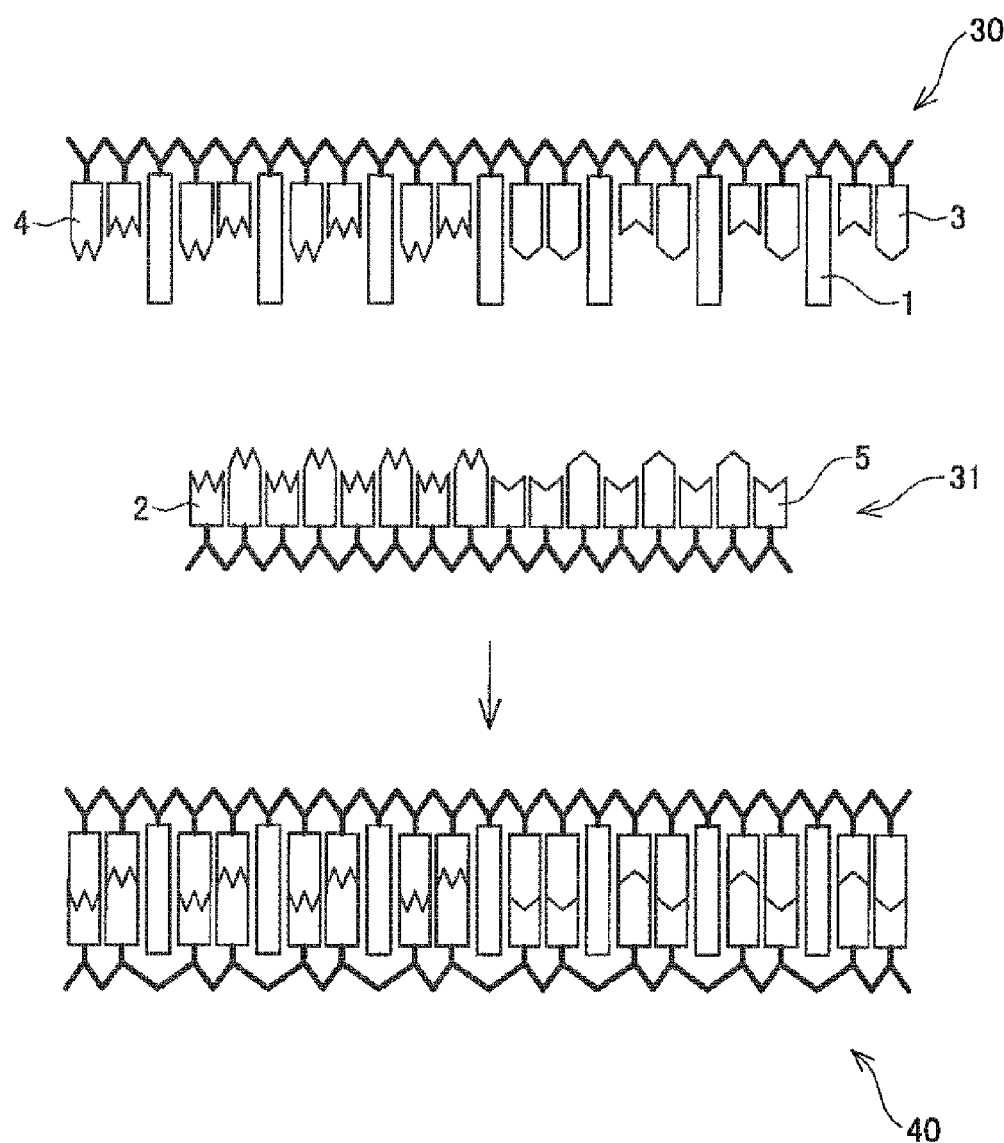
FIG. 4 is a conceptual view of a pair of oligonucleotides of a comparative example, and a complex thereof.

The modes of strand association are shown in the third column from the left in Table 4. "Associative" means cases in which as shown in FIG. 3, the complex is formed in such a way that the residues containing the methylthioazobenzenes in each of the pair of oligonucleotides associate with one another. "Wedge-shaped" means cases in which, as shown in FIG. 4, the complex is formed so that the residues containing the methylthioazobenzenes are arranged independently in a wedge shape in the sequence of complementary natural nucleotides. In FIG. 4, the oligonucleotides 30, 31 having paired complementary structures are provided with residues 1 of the azobenzene derivative shown in Formula (4a) above, complementary natural nucleotides 2, 4, and complementary natural nucleotides 3, 5. When the pair of oligonucleotides 30, 31 form complex 40, residues 1 are incorporated one by one as wedges between pairs of complementary bound nucleotides.

As shown in Table 4, the change (ΔTm) in Tm accompanying trans-cis isomerization in the wedge-shaped (1a-S/1b-0) Comparative Example 3-2 was 0.9° C., and there was very little photo-control ability. By contrast, in the associative type (1a-S/1b-S) of Example 3-1 there was a large ΔTm of 9.3° C. Sufficient photo-control ability was obtained even when hybridizing an oligonucleotide 1a-S and an oligonucleotide 1b-S each containing one S residue, so that there was only one pair of associating S residues. In the associative type (A4S/B4S) of Example 3-2, an extremely large ΔTm of 54.0° C. or higher was obtained. These results show that photo-control ability increases dramatically when the number of associations between residues S is increased. Almost perfect On-Off photo-control of double-chain formation and dissociation was achieved by increasing the number of residue S associations.

Example 4

In Example 4, an oligonucleotide containing cyclohexylthioazobenzene as shown in Formula (3b) below is explained as an example of the oligonucleotide represented by Formula (3) above.

[C18]

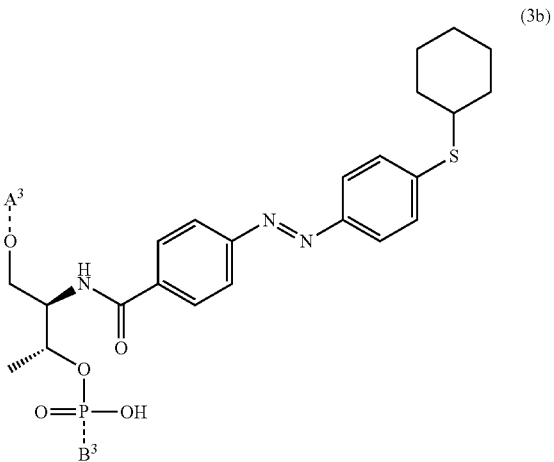
(3b)

(Synthesis of Oligonucleotide Containing Cyclohexylthioazobenzene)

An oligonucleotide containing cyclohexylthioazobenzene as shown in Formula (3b) below was synthesized according to the scheme shown in Formula (20) below. The Compounds 1-1-1 to 1-1-6 used in synthesis are shown in Formula (20) below. Compounds 1-1-2 to 1-1-6 constitute one example of the azobenzene derivative of Formula (14) above.

[C19]
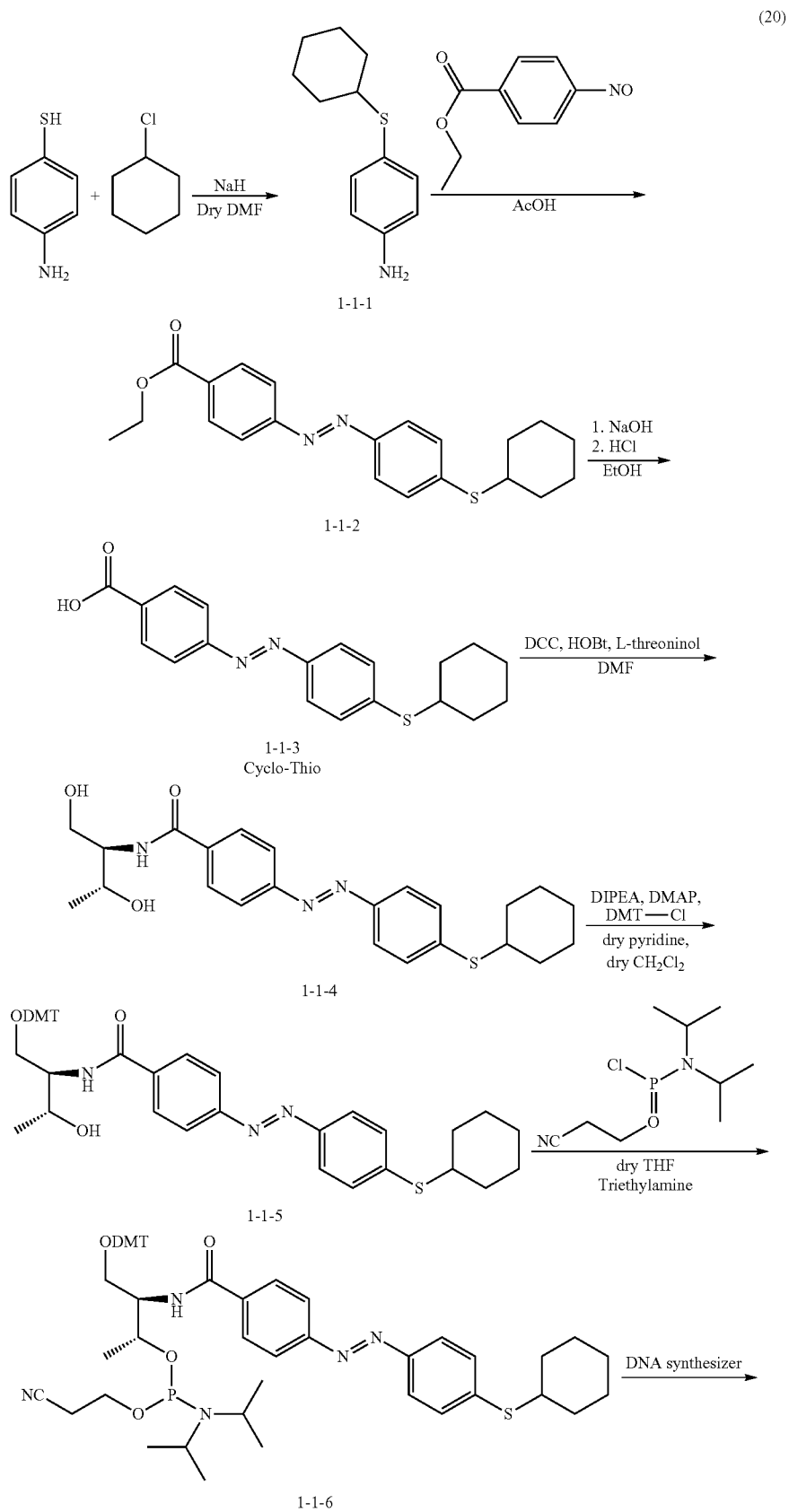
(20)

-continued

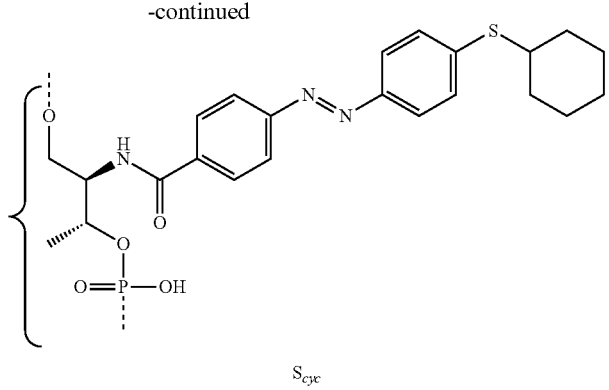

$S_{cyc}$ (Synthesis of Compound 1-1-1)

0.64 g (5 mmol) of 4-aminobenzenethiol was dissolved in about 10 mL of dehydrated dimethylformamide in a nitrogen atmosphere, 0.19 g (8 mmol) of sodium hydride was added little by little in an ice bath, and this was agitated 30 minutes as is. Ice bath cooling was continued as 0.79 mL of chloro-cyclohexane was dripped in, after which the ice bath was removed and the mixture was returned to room temperature and reacted overnight. This was then concentrated under reduced pressure, vacuum dried, and purified by silica gel column chromatography (hexane:ethyl acetate 3:1, triethy-lamine 3 vol % developing solvent) to obtain a Compound 1-1-1. 0.58 g (2.8 mmol) was obtained, with a yield of 56%.

(Synthesis of Compound 1-1-2)

0.58 g (2 mmol) of the Compound 1-1-1 and 0.6 g (1.2 eq.) of ethyl-p-nitrosobenzoate were dissolved in chloroform, and reacted overnight at room temperature after addition of 10 mL acetic acid. This was concentrated under reduced pressure, vacuum dried, and purified by silica gel column chromatography (hexane:ethyl acetate 3:1 developing solvent) to obtain a Compound 1-1-2. 0.65 g (1.77 mmol) was obtained, with a yield of 63%.

(Synthesis of Compound 1-1-3)

0.65 of the Compound 1-1-2 was dissolved in ethanol, made basic by addition of sodium hydroxide, and hydrolyzed for 3 days. This was then made acidic by addition of hydrochloric acid, the reaction was confirmed by thin-layer chromatography, and the solution was concentrated under reduced pressure, extracted with ethyl acetate, and separated (one time with distilled water, two times with sodium chloride). The organic layer was dried with magnesium sulfate, filtered, concentrated under reduced pressure, and vacuum dried to obtain a Compound 1-1-3. 0.52 g (1.22 mmol) was obtained, with a yield of 92%.

(Synthesis of Compound 1-1-4)

0.45 of the Compound 1-1-3, 0.15 g (1.1 eq.) of 1-threoninol and 0.24 g (1.2 eq.) of 1-hydroxybenzotriazole were placed in a flask, and dissolved in dimethylformamide. Next, 0.32 g (1.55 mmol) of dicyclohexyl carbodiimide was taken in a beaker, and dissolved in dimethylformamide. The solution of dissolved dicyclohexyl carbodiimide was dripped slowly into the flask, and reacted overnight. The solids were then removed by filtration, and the filtrate was concentrated under reduced pressure, vacuum dried, and purified by silica gel column chromatography (chloroform:methanol=9:1 developing solvent) to obtain a Compound 1-1-4. 0.52 g (1.22 mmol) was obtained, with a yield of 92%.

(Synthesis of Compound 1-1-5)

The Compound 1-1-4 was placed in a two-necked flask, nitrogen substituted, and dissolved in 8 mL of dehydrated pyridine. 0.25 mL (1.2 eq.) of N,N-diisopropylethylamine was added to this. 0.50 g (1.2 eq.) of dimethoxytrityl chloride and 0.03 g (1.2 eq.) of N,N-dimethyl-4-aminopyridine were placed in a separate flask, nitrogen substituted, and dissolved in dehydrated dichloromethane. The solution in the flask with the dissolved dimethoxytrityl chloride was dripped slowly into the solution in the two-necked flask containing the Compound 1-1-4 in an ice bath. This was then reacted as is for 2 hours in the ice bath. The progress of the reaction was confirmed by thin-layer chromatography, and the solution was azeotroped two times with toluene, vacuum dried, and purified by silica gel column chromatography (hexane:ethyl acetate=1:1, triethylamine=3 vol % developing solvent) to obtain a Compound 1-1-5. 0.52 g (0.71 mmol) was obtained, with a yield of 58%.

(Synthesis of Compound 1-1-6)

0.15 g of the Compound 1-1-5 was placed in a two-necked flask, nitrogen substituted, and dissolved in a suitable amount of dehydrated tetrahydrofuran. 0.25 mL (5 eq.) of triethylamine was then added, the solution was placed in an ice bath, 0.16 mL of an amiditing reagent (2-cyanoethyl N,N,N'N'-tetraisopropyl phosphoramidite) was added, the ice bath was removed, and the solution was reacted for a further 1 hour at room temperature. This was extracted with ethyl acetate, separated one time with saturated aqueous sodium bicarbonate solution and one time with saturated aqueous sodium chloride solution, dried with magnesium sulfate, filtered, concentrated under reduced pressure, vacuum dried, and azeotroped with dehydrated acetonitrile to obtain a Compound 1-1-6. The yield was about 100%.

The Compound 1-1-6 is an amidite monomer. An oligonucleotide containing the cyclohexylthioazobenzene residue (Scyc) shown in Formula (20) above was synthesized using the Compound 1-1-6 with a DNA synthesizer.

Example 5

In Example 5, an oligonucleotide containing adamantylthioazobenzene as shown in Formula (3c) below is explained as an example of the oligonucleotide represented by Formula (3) above.

[C20]

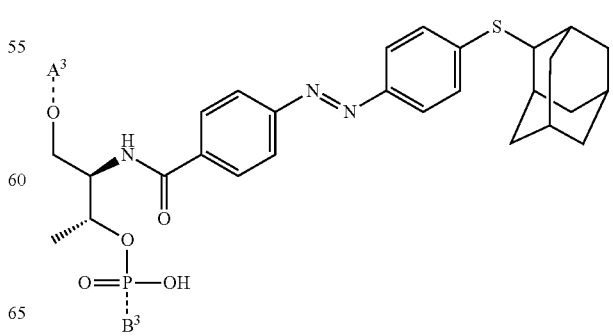

(3c)

(Synthesis of oligonucleotide containing adamantylthioazobenzene)

An oligonucleotide containing adamantylthioazobenzene as shown in Formula (3b) above was synthesized according to the scheme of Formula (21) below. The Compounds 2-1-1 to 2-1-6 used in synthesis are shown in the Formula (21) below. The Compounds 2-1-2 to 2-1-6 constitute one example of the azobenzene derivative of Formula (14) above.

[C21]

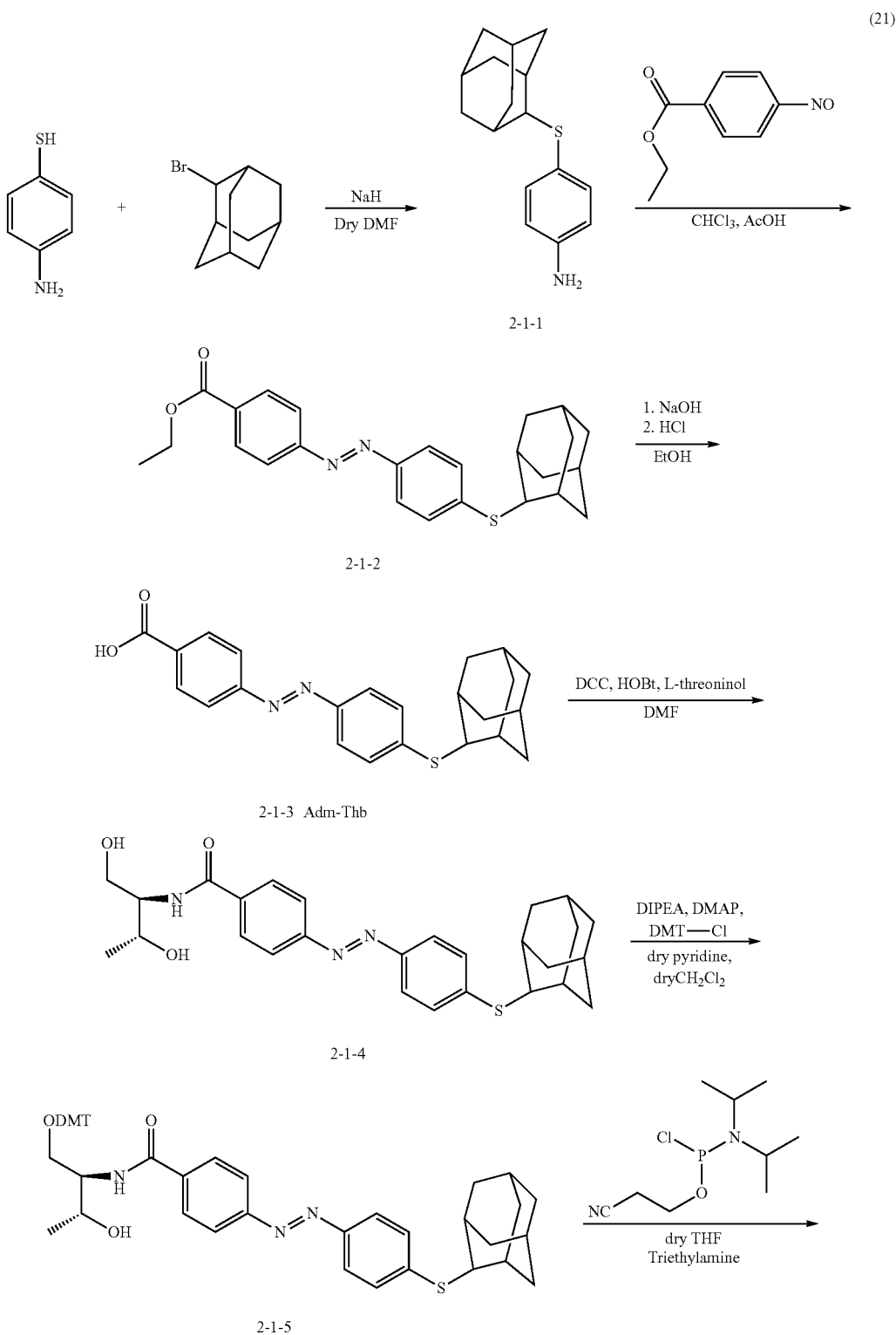

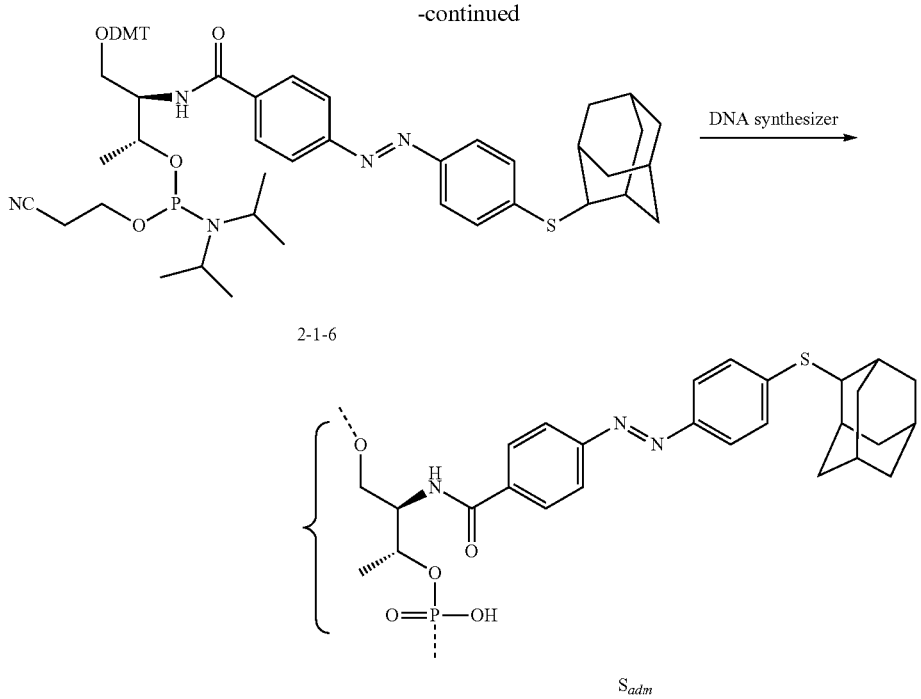

2-1-6

$S_{adm}$ (Synthesis of Compound 2-1-1)

1.56 g (12.4 mmol) of 4-aminobenzenethiol was dissolved in 12 mL of dehydrated dimethylformamide in a nitrogen atmosphere, 0.19 g (8 mmol) of sodium hydride was added little by little in an ice bath, and this was agitated as is for 30 minutes. A dimethylformamide solution of bromoadamantane was dripped in with ice bath cooling, the ice bath was removed, and the solution was returned to room temperature and reacted for 2 days. The reaction was confirmed by thin-layer chromatography, and the solution was concentrated under reduced pressure, vacuum dried, separated with saturated aqueous sodium bicarbonate solution and saturated aqueous sodium chloride solution, and finally purified by silica gel column chromatography (hexane:ethyl acetate=4:1, triethylamine 3 vol % developing solvent) to obtain a Compound 2-1-1. 6.9 mmol was obtained, with a yield of 56%.

(Synthesis of Compound 2-1-2)

1.79 g (6.9 mmol) of the Compound 2-1-1 and 1.36 g (1.2 eq.) of ethyl-p-nitrosobenzoate were dissolved in glacial acetic acid, and agitated for 2 hours. The reaction was confirmed by thin-layer chromatography, and the mixture was concentrated under reduced pressure, vacuum dried, and dissolved in ethyl acetate before being washed two times with saturated aqueous sodium bicarbonate solution and one time with saturated aqueous sodium chloride solution, dried with magnesium sulfate, concentrated under reduced pressure, vacuum dried, and purified by silica gel column chromatography (hexane:ethyl acetate=18:1 developing solvent) to obtain a Compound 2-1-2.

(Synthesis of Compound 2-1-3)

0.65 of the Compound 2-1-2 was dissolved in ethanol, made basic by addition of sodium hydroxide, and hydrolyzed for 3 days. This was then made acidic by addition of hydrochloric acid, the reaction was confirmed by thin-layer chromatography, and the solution was concentrated under reduced pressure, extracted with ethyl acetate, and washed (one time with distilled water, two times with sodium chloride). The organic layer was dried with magnesium sulfate, filtered, concentrated under reduced pressure, and vacuum dried to obtain a Compound 2-1-3.

(Synthesis of Compound 2-1-4)

1.0 g of the Compound 2-1-3, 0.29 g (1.1 eq.) of L-threoninol and 0.47 g (1.2 eq.) of 1-hydroxybenzotriazol were placed in a flask, and dissolved in dimethylformamide. Next, 0.63 g (1.2 mmol) of dicyclohexyl carbodiimide was placed in a beaker, and dissolved in dimethylformamide. The solution of dissolved dicyclohexyl carbodiimide was dripped slowly into the flask, and reacted overnight. The solids were then removed by filtration, and the filtrate was concentrated under reduced pressure, vacuum dried, and purified by silica gel column chromatography (chloroform:methanol=15:1 developing solvent) to obtain a Compound 2-1-4. The yield was about 100%.

(Synthesis of Compound 2-1-5)

Compound 2-1-4 was placed in a two-necked flask, nitrogen substituted, and dissolved in dehydrated pyridine. 0.63 mL of N,N-diisopropylethylamine was then added thereto. 1.25 g (1.2 eq.) of dimethoxytrityl chloride and 0.75 g (0.2 eq.) of N,N-dimethyl-4-aminopyridine were then taken in a separate flask, nitrogen substituted, and dissolved in dehydrated dichloromethane. The solution in the flask with the dissolved dimethoxytrityl chloride was dripped into the solution in the two-necked flask with the Compound 1-1-4 in an ice bath, and reacted for 2 hours as is in the ice bath. The progress of the reaction was confirmed by thin-layer chromatography, and the solution was azeotroped two times with toluene, vacuum dried, and purified by silica gel column chromatography (hexane:ethyl acetate=1:1, triethylamine=3 vol % developing solvent) to obtain a Compound 2-1-5. 1.44 g (1.84 mmol) was obtained, with a yield of 59.8%.

(Synthesis of Compound 2-1-6)

0.23 g of the Compound 2-1-5 was placed in a two-necked flask, nitrogen substituted, and dissolved in a suitable amount of dehydrated tetrahydrofuran. After addition of 0.21 mL (5 eq.) of triethylamine, this was placed in an ice bath, 0.13 mL of an amiditing reagent (2-cyanoethyl N,N,N',N'-tetraisopropyl phosphoramidite) was added, the ice bath was removed, and the solution was reacted for 1 hour at room temperature. This was then extracted with ethyl acetate, separated one time with saturated aqueous sodium bicarbonate solution and one time with saturated aqueous sodium chloride solution, dried with magnesium sulfate, filtered, concentrated under reduced pressure, vacuum dried, and purified by silica gel column chromatography (hexane:ethyl acetate=1:1, triethylamine=3 vol % developing solvent) to obtain a Compound 2-1-6. The yield was about 100%.

The Compound 2-1-6 is an amidite monomer. An oligonucleotide containing a cyclohexylthioazobenzene residue (Sadm) as shown in Formula (21) above was synthesized using the Compound 2-1-6 with a DNA synthesizer.

The synthesized sequences are shown below.

```
                                              (SEQ ID NO: 1)
1a-X:  5'-GGTATCXGCAATC-3'  (X = Scyc, Sadm)

(SEQ ID NO: 2)
1b-0:  3'-CCATAGCGTTAG-5'
```

(Evaluation of Photo-Control Ability)
(UV-Vis Spectrum)
The 1a-Scyc of Example 4 and the 1a-Sadm of Example 5 were shown to have maximum absorption near 400 nm.
(Evaluation of ΔTm)
The melting temperatures Tm of the 1a-X/1b-0 double strands were measured next. In the case of X=Scyc (Example 4) and Sadm (Example 5), trans-to-cis isomerization was performed by irradiating for 10 minutes with xenon lamp light passed through a 400 nm interference filter, with the temperature of the solution maintained at 60° C. Isomerization of 60% or more into the cis-form was by this operation was confirmed from the absorption spectrum. Table 5 shows changes in melting temperature accompanying photo-isomerization of the 1a-X/1b-0 double strand. Measurement was performed under conditions of oligonucleotide concentration 5 μM, sodium chloride concentration 100 mM, pH 7.0 (10 mM phosphate buffer). In Examples 4 and 5, the ΔTm values are negative because the cis-isomer is more stable than the trans-isomer.

TABLE 5

| | | Melting temperature Tm/° C. | | |
|---|---|---|---|---|
| | X | Trans-form | Cis-form | ΔTm/° C. |
| Example 4 | Scyc | 41.6 | 47.6 | −6.0 |
| Example 5 | Sadm | 39.7 | 45.2 | −5.5 |

As shown in Tables 3 and 5, the absolute value of ΔTm was greater and photo-control ability was higher with the oligonucleotide having cyclohexylthioazobenzene of Example 4 and the oligonucleotide having adamantylthioazobenzene of Example 5 than with the oligonucleotide having isopropylthioazobenzene of Example 2. With the oligonucleotides having cyclic hydrocarbon groups of Example 4 and Example 5, the absolute value of ΔTm is greater than with the linear hydrocarbon of Example 2, and it is possible to provide an oligonucleotide with high photo-control ability.

Examples of the present invention were explained above, but these are only examples, and the Claims are not limited thereby. The technology described in the claims encompasses various changes and modification to the specific examples given above.

The technical elements explained in the Description or the drawings are technically useful individually and in various combinations, and their utility is not limited to the combinations described in the Claims of the original application. Moreover, the technology disclosed in the Description or drawings can achieve multiple objects simultaneously, and has technical utility by virtue of achieving any one of those objects.

Sequence Table Free Text
SEQ ID NOS:1 to 6 Synthetic oligonucleotides
[Sequence Table]

The invention claimed is:

1. An oligonucleotide containing an azobenzene derivative, represented by Formula (1) or (2) below:

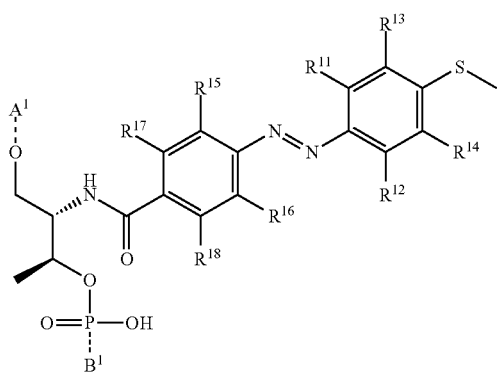

(1)

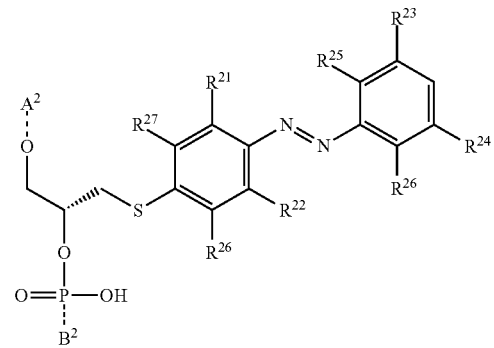

(2)

where:
- $A^1$ and $A^2$ each independently represents a hydrogen atom, nucleotide or oligonucleotide,
- $B^1$ and $B^2$ each independently represents hydroxyl groups, nucleotides or oligonucleotides,
- $R^{11}$ and $R^{12}$ each independently represents a $C_{1-20}$ alkyl group,
- $R^{21}$ and $R^{22}$ each independently represents a hydrogen atom or $C_{1-20}$ alkyl group, and
- $R^{13}$ to $R^{18}$ and $R^{23}$ to $R^{28}$ each independently represents a hydrogen atom; a $C_{1-20}$ alkyl group or alkoxy group optionally substituted with a halogen atom, hydroxyl group, amino group, nitro group or carboxyl group; a $C_{2-20}$ alkenyl group or alkynyl group optionally substituted with a halogen atom, hydroxyl group, amino group, nitro group or carboxyl group; a hydroxyl group; a halogen atom; an amino group; a nitro group; or a carboxyl group.

2. The oligonucleotide according to claim 1, wherein $R^{13}$ to $R^{18}$ and $R^{23}$ to $R^{28}$ are hydrogen atoms.

3. The oligonucleotide according to claim 1, wherein $R^{11}$ and $R^{12}$ are methyl groups.

4. An oligonucleotide containing an azobenzene derivative represented by Formula (3) below:

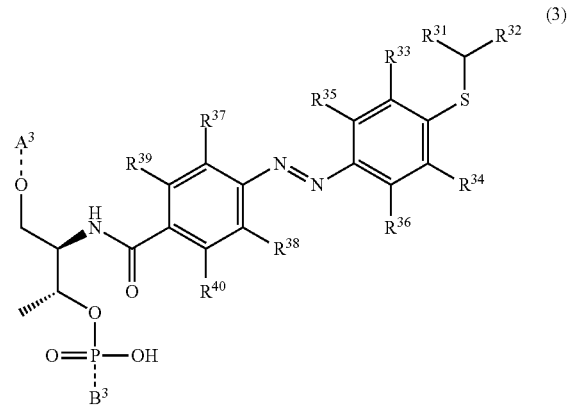

(3)

where:
- $A^3$ represents a hydrogen atom, nucleotide, or oligonucleotide,
- $B^3$ represents a hydroxyl group, nucleotide, or oligonucleotide,
- $R^{31}$ and $R^{32}$ each independently represents a $C_{1-20}$ alkyl group, or $R^{31}$ and $R^{32}$ bind with each other to represent a $C_{5-40}$ cyclic alkyl or aryl group together with a carbon atom for binding to a sulfur atom, and
- $R^{33}$ to $R^{40}$ each independently represents a hydrogen atom; a $C_{1-20}$ alkyl or alkoxy group optionally substituted with a halogen atom, hydroxyl group, amino group, nitro group or carboxyl group; a $C_{2-20}$ alkenyl or alkynyl group optionally substituted with a halogen atom, hydroxyl group, amino group, nitro group or carboxyl group; a hydroxyl group; a halogen atom; an amino group; a nitro group; or a carboxyl group.

5. The oligonucleotide according to claim 4, wherein $R^{31}$ and $R^{32}$ bind with each other to represent a cyclohexyl group or adamantyl group together with a carbon atom for linking to a sulfur atom.

6. The oligonucleotide according to claim 4, wherein:
- $R^{31}$ and $R^{32}$ each independently represents a $C_{1-4}$ alkyl group, and
- $R^{33}$ to $R^{44}$ are hydrogen atoms.

7. The oligonucleotide according to claim 6, wherein $R^{31}$ and $R^{32}$ are methyl groups.

8. A photo-switching agent, by which the formation and dissociation of a double strand can be controlled by visible light irradiation, and which is provided with the oligonucleotide according to claim 1.

9. A photo-switching agent, by which the formation and dissociation of a double strand can be controlled by visible light irradiation, and which is provided with a pair of oligonucleotides having complementary sequences that form a complex, with each of the pair of oligonucleotides being provided with at least one azobenzene derivative represented by Formula (2) or (4) below in a pairing position:

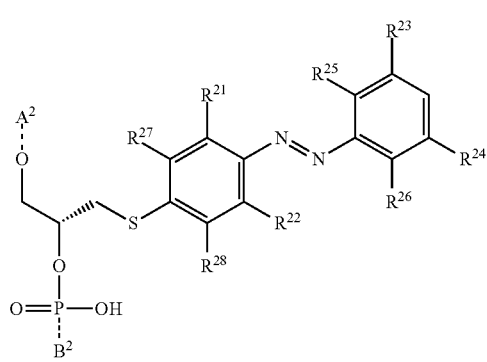

(2)

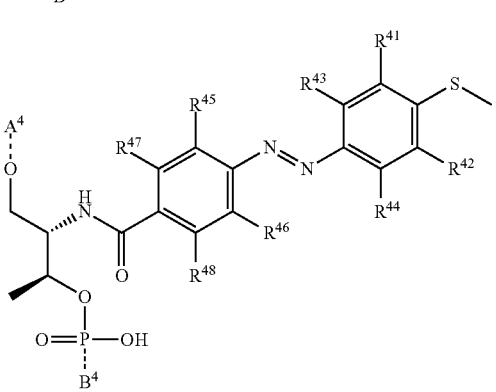

(4)

where:
A² and A⁴ each independently represents a hydrogen atom, nucleotide or oligonucleotide,
B² and B⁴ each independently represents a hydroxyl group, nucleotide or oligonucleotide,
$R^{21}$ and $R^{22}$ each independently represents a hydrogen atom or $C_{1-20}$ alkyl group, and
$R^{23}$-$R^{28}$ and $R^{41}$ to $R^{48}$ each independently represents a hydrogen atom; a $C_{1-20}$ alkyl group or alkoxy group optionally substituted with a halogen atom, hydroxyl group, amino group, nitro group or carboxyl group; a $C_{2-20}$ alkenyl or alkynyl group optionally substituted with a halogen atom, hydroxyl group, amino group, nitro group or carboxyl group; a hydroxyl group; a halogen atom; an amino group; a nitro group; or a carboxyl group.

10. The photo-switching agent according to claim 9, wherein $R^{43}$ and $R^{44}$ represent methyl groups or hydrogen atoms, and $R^{41}$, $R^{42}$ and $R^{45}$ to $R^{48}$ are hydrogen atoms.

11. The photo-switching agent according to claim 9, wherein each of the pair of oligonucleotides has two or more of the azobenzene derivative adjacent to one another on either side of two or more nucleotides.

12. An azobenzene derivative represented by Formula (11) below:

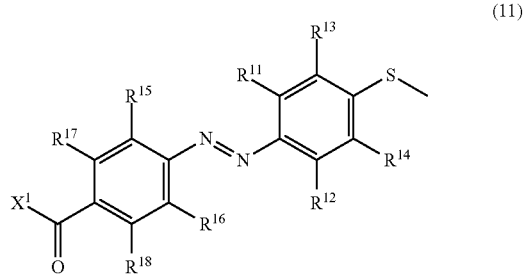

(11)

where:
X¹ represents either a hydroxyl group or a group represented by Formula (12) below,
$R^{11}$ and $R^{12}$ each independently represents a $C_{1-20}$ alkyl group, and
$R^{13}$ to $R^{18}$ each independently represents a hydrogen atom; a $C_{1-20}$ alkyl group or alkoxy group optionally substituted with a halogen atom, hydroxyl group, amino group, nitro group or carboxyl group; a $C_{2-20}$ alkenyl or alkynyl group optionally substituted with a halogen atom, hydroxyl group, amino group, nitro group or carboxyl group; a hydroxyl group; a halogen atom; an amino group; a nitro group; or a carboxyl group;

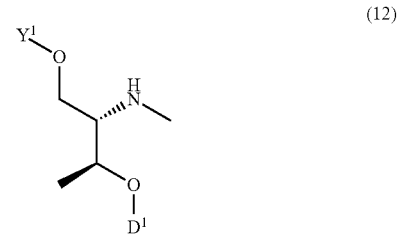

(12)

where:
Y¹ represents a hydrogen atom or hydroxyl protecting group, and
D¹ represents a hydrogen atom, a hydroxyl protecting group, a phosphoramidite group or a linking group that is bound or to be bound to a solid-phase carrier; and
wherein when X¹ is a group represented by Formula (12), the N in Formula (12) is bonded to the C═O in the azobenzene derivative represented by Formula (11) in place of X¹.

13. An azobenzene derivative represented by Formula (13) below:

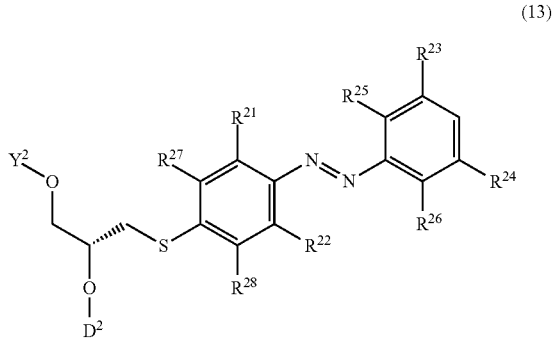

(13)

where:
- $Y^2$ represents a hydrogen atom or hydroxyl protecting group,
- $D^2$ represents a hydrogen atom, a hydroxyl protecting group, a phosphoramidite group or a linking group that is bound or to be bound to a solid-phase carrier,
- $R^{21}$ and $R^{22}$ each independently represents a hydrogen atom or $C_{1-20}$ alkyl group, and
- $R^{23}$ to $R^{28}$ each independently represents a hydrogen atom; a $C_{1-20}$ alkyl group or alkoxy group optionally substituted with a halogen atom, hydroxyl group, amino group, nitro group or carboxyl group; a $C_{2-20}$ alkenyl or alkynyl group optionally substituted with a halogen atom, hydroxyl group, amino group, nitro group or carboxyl group; a hydroxyl group; a halogen atom; an amino group; a nitro group; or a carboxyl group.

14. An azobenzene derivative represented by Formula (14) below:

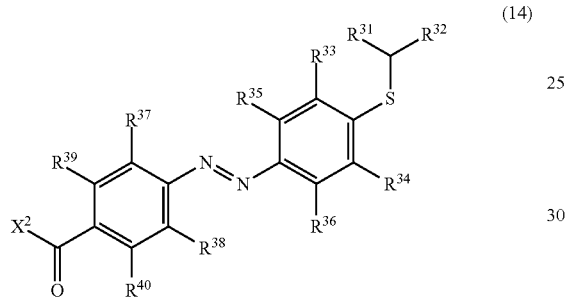

(14)

where:
- $X^2$ represents a hydroxy group or a group represented by Formula (15) below,
- $R^{31}$ and $R^{32}$ each independently represents a $C_{1-20}$ alkyl group, or $R^{31}$ and $R^{32}$ bind with each other to represent a $C_{5-40}$ cyclic alkyl group or aryl group together with a carbon atom for linking to a sulfur atom, and
- $R^{33}$ to $R^{40}$ each independently represents a hydrogen atom; a $C_{1-20}$ alkyl group or alkoxy group optionally substituted with a halogen atom, hydroxyl group, amino group, nitro group or carboxyl group; a $C_{2-20}$ alkenyl or alkynyl group optionally substituted with a halogen atom, hydroxyl group, amino group, nitro group or carboxyl group; a hydroxyl group; a halogen atom; an amino group; a nitro group; or a carboxyl group;

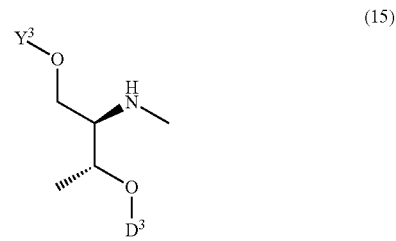

(15)

where:
- $Y^3$ represents a hydrogen atom or hydroxyl protecting group, and
- $D^3$ represents a hydrogen atom or hydroxyl protecting group, a phosphoramidite group, or a linking group that is bound or to be bound to a solid-phase carrier; and wherein when $X^2$ is a group represented by Formula (15), the N in Formula (15) is bonded to the C=O in the azobenzene derivative represented by Formula (15) in place of $X^2$.

* * * * *

SEQUENCE LISTING

```
<160> NUMBER OF SEQ ID NOS: 6

<210> SEQ ID NO 1
<211> LENGTH: 13
<212> TYPE: DNA
<213> ORGANISM: Artificial Sequence
<220> FEATURE:
<223> OTHER INFORMATION: Synthetic construct - Synthetic Oligonucleotide
<220> FEATURE:
<221> NAME/KEY: misc_feature
<222> LOCATION: (7)..(7)
<223> OTHER INFORMATION: n is any nucleotide anologue containing an
      azobenzene group

<400> SEQUENCE: 1
ggtatcngca atc                                                         13

<210> SEQ ID NO 2
<211> LENGTH: 12
<212> TYPE: DNA
<213> ORGANISM: Artificial Sequence
<220> FEATURE:
<223> OTHER INFORMATION: Synthetic construct - Synthetic Oligonucleotide

<400> SEQUENCE: 2
gattgcgata cc                                                          12
```

<210> SEQ ID NO 3
<211> LENGTH: 12
<212> TYPE: DNA
<213> ORGANISM: Artificial Sequence
<220> FEATURE:
<223> OTHER INFORMATION: Synthetic construct - Synthetic Oligonucleotide

<400> SEQUENCE: 3
ggtatcgcaa tc                                                           12

<210> SEQ ID NO 4
<211> LENGTH: 13
<212> TYPE: DNA
<213> ORGANISM: Artificial Sequence
<220> FEATURE:
<223> OTHER INFORMATION: Synthetic construct - Synthetic Oligonucleotide
<220> FEATURE:
<221> NAME/KEY: misc_feature
<222> LOCATION: (7)..(7)
<223> OTHER INFORMATION: n is any nucleotide anologue containing an
      azobenzene group

<400> SEQUENCE: 4
gattgcngat acc                                                          13

<210> SEQ ID NO 5
<211> LENGTH: 14
<212> TYPE: DNA
<213> ORGANISM: Artificial Sequence
<220> FEATURE:
<223> OTHER INFORMATION: Synthetic construct - Synthetic Oligonucleotide
<220> FEATURE:
<221> NAME/KEY: misc_feature
<222> LOCATION: (3)..(3)
<223> OTHER INFORMATION: n is any nucleotide anologue containing an
      azobenzene group
<220> FEATURE:
<221> NAME/KEY: misc_feature
<222> LOCATION: (6)..(6)
<223> OTHER INFORMATION: n is any nucleotide anologue containing an
      azobenzene group
<220> FEATURE:
<221> NAME/KEY: misc_feature
<222> LOCATION: (9)..(9)
<223> OTHER INFORMATION: n is any nucleotide anologue containing an
      azobenzene group
<220> FEATURE:
<221> NAME/KEY: misc_feature
<222> LOCATION: (12)..(12)
<223> OTHER INFORMATION: n is any nucleotide anologue containing an
      azobenzene group

<400> SEQUENCE: 5
cgnttnagnt tnca                                                         14

<210> SEQ ID NO 6
<211> LENGTH: 14
<212> TYPE: DNA
<213> ORGANISM: Artificial Sequence
<220> FEATURE:
<223> OTHER INFORMATION: Synthetic construct - Synthetic Oligonucleotide
<220> FEATURE:
<221> NAME/KEY: misc_feature
<222> LOCATION: (3)..(3)
<223> OTHER INFORMATION: n is any nucleotide anologue containing an
      azobenzene group
<220> FEATURE:
<221> NAME/KEY: misc_feature
<222> LOCATION: (6)..(6)
<223> OTHER INFORMATION: n is any nucleotide anologue containing an
      azobenzene group

```
<220> FEATURE:
<221> NAME/KEY: misc_feature
<222> LOCATION: (9)..(9)
<223> OTHER INFORMATION: n is any nucleotide anologue containing an
      azobenzene group
<220> FEATURE:
<221> NAME/KEY: misc_feature
<222> LOCATION: (12)..(12)
<223> OTHER INFORMATION: n is any nucleotide anologue containing an
      azobenzene group

<400> SEQUENCE: 6
tgnaanctna ancg                                                     14
```